US009676779B2

(12) United States Patent
Schwiebert et al.

(10) Patent No.: US 9,676,779 B2
(45) Date of Patent: Jun. 13, 2017

(54) SMALL MOLECULE CFTR CORRECTORS

(71) Applicant: DISCOVERYBIOMED, INC., Birmingham, AL (US)

(72) Inventors: Erik Schwiebert, Birmingham, AL (US); John Streiff, Birmingham, AL (US); John Dixon, Leicestershire (GB); Hongwu Gao, Shanghai (CN)

(73) Assignee: DiscoveryBiomed, Inc., Birmingham, AL (US)

( * ) Notice: Subject to any disclaimer, the term of this patent is extended or adjusted under 35 U.S.C. 154(b) by 0 days.

(21) Appl. No.: 14/646,063

(22) PCT Filed: Nov. 20, 2013

(86) PCT No.: PCT/US2013/070987
§ 371 (c)(1),
(2) Date: May 20, 2015

(87) PCT Pub. No.: WO2014/081820
PCT Pub. Date: May 30, 2014

(65) Prior Publication Data
US 2015/0299206 A1 Oct. 22, 2015

Related U.S. Application Data

(60) Provisional application No. 61/728,414, filed on Nov. 20, 2012.

(51) Int. Cl.
*C07D 471/04* (2006.01)
*C07D 487/04* (2006.01)
*C07D 498/04* (2006.01)

(52) U.S. Cl.
CPC ......... *C07D 487/04* (2013.01); *C07D 471/04* (2013.01); *C07D 498/04* (2013.01)

(58) Field of Classification Search
CPC ... C07D 471/04; C07D 487/04; C07D 498/04
See application file for complete search history.

(56) References Cited

U.S. PATENT DOCUMENTS

| 5,084,457 | A | 1/1992 | Fanshawe et al. |
|---|---|---|---|
| 5,650,096 | A | 7/1997 | Harris et al. |
| 6,248,753 | B1 | 6/2001 | Chen |
| 8,642,660 | B2 | 2/2014 | Goldfarb |
| 2005/0209255 | A1 | 9/2005 | Jimenez et al. |
| 2007/0275986 | A1 | 11/2007 | Becq et al. |
| 2009/0048260 | A1 | 2/2009 | Becq et al. |
| 2009/0163545 | A1 | 6/2009 | Goldfarb |
| 2010/0190832 | A1 | 7/2010 | Surolia |
| 2011/0146381 | A1 | 6/2011 | Wells et al. |

FOREIGN PATENT DOCUMENTS

| EP | 1505068 A1 | 2/2005 | | |
|---|---|---|---|---|
| FR | 2116302 | 7/1972 | | |
| FR | 2910001 | 3/2009 | | |
| JP | 55066580 | 5/1980 | | |
| JP | 62230782 | * 9/1987 | ............... | G21C 3/06 |
| SU | 1235867 | 6/1986 | | |
| WO | 9837878 | 9/1998 | | |
| WO | 0043373 | 7/2000 | | |
| WO | 0061159 | 10/2000 | | |
| WO | 03037345 A1 | 5/2003 | | |
| WO | 03066630 | 8/2003 | | |
| WO | 2004020596 | 3/2004 | | |
| WO | 2007044560 | 4/2007 | | |
| WO | 2009036341 | 3/2009 | | |
| WO | WO 2011/014520 | * 2/2011 | ........... | C07D 487/04 |
| WO | 2011046381 | 4/2011 | | |
| WO | 2012075393 | 6/2012 | | |
| WO | 2012145981 A1 | 11/2012 | | |
| WO | 2012158913 | 11/2012 | | |
| WO | 2012158913 A2 | 11/2012 | | |
| WO | 2012171954 | 12/2012 | | |
| WO | 2013052844 | 4/2013 | | |
| WO | 2014081820 | 5/2014 | | |
| WO | 2014081821 | 5/2014 | | |
| WO | 2014152213 | 9/2014 | | |
| WO | 2014152278 | 9/2014 | | |

OTHER PUBLICATIONS

Wolff, Manfred E., Burger's Medicinal Chemistry and Drug Discovery, Fifth Ed., vol. 1: Principles and Practice, John Wiley & Sons, 1995, 975.*
Banker, Gilbert S. et al., Modem Pharmaceutics, Marcel Dekker, New York, 1996.*
Lack, et al., Targeting the Binding Function 3 (BF3) Site of the Human Androgen Receptor through Virtual Screening, J. Med. Chem., 55, 565 (2012).*
Abdelhamid, et al, A New Approach for the Synthesis of Some Pyrazolo[1,5-c]triazines and Pyrazolo[1,5-a]pyrimidines Containing Naphtofuran Moiety, J. Het. Chem., 49, 116 (2012).*
Didenko, et al., First example of an ANRORC rearrangement of pyrazolo[5,1-c][1,2,4]triazine involving a side chain, Chemistry of Heterocyclic Compounds, 46(6), 770-772 (2010).*
Mohamed, et al, Synthesis of some new pyridones, fused pyrimidines, and fused 1,2,4-triazines, J. of Het. Chem. 47(3), 517-523 (2010).*
Shikhaliev, et al, Pyrazole-3(5)-diazonium salts in the synthesis of novel pyrazolo[5,1-c][1,2,4]triazines, Russian Chemical Bulletin 58(5), 1034-1040 (2009).*

(Continued)

*Primary Examiner* — Erich A Leeser
(74) *Attorney, Agent, or Firm* — Kilpatrick Townsend & Stockton LLP

(57) ABSTRACT

Novel CFTR corrector compounds that are effective in rescuing halide efflux, delF508-CFTR protein processing, and apical functional chloride ion transport in a cell are provided. Also provided are methods for treating protein folding disorders (e.g., cystic fibrosis). The methods include administering a CFTR corrector compound or pharmaceutically acceptable salt or prodrug thereof. Methods of rescuing halide efflux in a cell, correcting a processing defect of a delF508-CFTR protein in a cell, and correcting functional delF508-CFTR chloride channels in a cell are also provided.

20 Claims, 10 Drawing Sheets

(56) References Cited

OTHER PUBLICATIONS

Didenko, et al., Synthesis of 7,8-dihydro-6-pyrazolo[5',1':3,4][1,2,4]triazino[6,5-d][1,2]diazepine-6-one, a new heterocyclic system, Chemistry of Heterocyclic Compounds, 45(2), 248-249 (2009).*
Didenko, et al., Transformations of 3-alkyl-4-(methoxyphenyl)-1H-pyrazole-5-diazonium salts, Russian J. of Org. Chem. 45(2), 211-214, (2009).*
Shaaban, Microwave-assisted synthesis of fused heterocycles incorporating trifluoromethyl moiety, J. of Fluorine Chem. 129(12), 1156-1161, (2008).*
Abd El-Maksoud, S. A., Electrochemical studies on the effect of pyrazolo-containing compounds on the corrosion of carbon steel in 1 M sulphuric acid, Materials and Corrosion, 54(2), 106-112, (2003).*
Almansa, et al., Synthesis and SAR of a new series of COX-2-selective inhibitors: pyrazolo[1,5-a]pyrimidines, J. of Med. Chem., 44(3), 350-361, (2001).*
Sayed, et al., Synthesis and reactivity of cyanomethyl 2-amino-4-methylthiazolyl ketone. A facile synthesis of novel pyrazolo[5,1-c]-1,2,4-triazine, 1,2,4-triazolo[5,1-c]-1,2,4-triazine, 1,2,4-triazino[4,3-a]benzimidazole, pyridazin-6-imine and 6-oxopyridazinone derivatives, Heteroatom Chemistry (1999), 10(5), 385-390.*
Elnagdi et al., Reactions with heterocyclic amidines. VII. Synthesis of some new pyrazolo[1,5-c]-1,2,4-triazines, pyrazolo[1,5-a]-1,3,5-triazines and pyrazolo[1,5-a]pyrimidines, Monatshefte fuer Chemie (1981), 112(2), 245-52.*
Novinson, et al., Synthesis and Antimicrobial Activity of Some Novel Heterocycles. Azolo-as-triazines, J. of Med. Chem., vol. 19, No. 4, 517, (1976).*
[Online] STN, Registry, Jun. 24, 2005, compound with RN 1030421-22-7.*
[online] Registry via STN, RN 403721-73-3, Apr. 3, 2002.
[online] Registry via STN, RN 403721-74-4, Apr. 3, 2002.
[online] Registry via STN, RN 724744-64-3, Aug. 10, 2004.
STN, Registry, RN 903852-54-0, Aug. 23, 2006.
STN, Registry, RN 899737-99-6, Aug. 8, 2006.
STN, Registry, RN 899738-02-4, Aug. 8, 2006.
STN, Registry, RN 899948-04-0, Aug. 9, 2006.
STN, Registry, RN 899948-08-4, Aug. 9, 2006.
STN, Registry, RN 899948-10-8, Aug. 9, 2006.
STN, Registry, RN 899998-08-4, Aug. 9, 2006.
STN, Registry, RN 899998-18-6, Aug. 9, 2006.
STN, Registry, RN 799824-17-2, Dec. 20, 2004.
[online] Registry via STN, RN 313954-56-2, Jan. 15, 2001.
[online] Registry via STN, RN 313954-55-1, Jan. 15, 2001.
[online] Registry via STN, RN 312703-21-2, Jan. 4, 2001.
STN, Registry, RN 941951-07-01, Jul. 10, 2007.
STN, Registry, compound with RN 1030421-22-7, Jun. 24, 2008.
STN, Registry, RN 1015553-18-0, Jun. 24, 2008.
STN, Registry, RN 1030450-60-2, Jun. 24, 2008.
STN, Registry, RN 1030450-84-0, Jun. 24, 2008.
STN, Registry, RN 1030480-33-1., Jun. 25, 2008.
STN, Registry, RN 1030480-38-6, Jun. 25, 2008.
STN, Registry, RN 1030523-95-5, Jun. 25, 2008.
STN, Registry, RN 1030569-95-9, Jun. 25, 2008.
STN, Registry, RN 1030672-54-8, Jun. 25, 2008.
[online] Registry via STN, RN 325473-18-5, Mar. 4, 2001.
[online] Registry via STN, RN 325804-06-6, Mar. 6, 2001.
[online] Registry via STN, RN 325804-07-7, Mar. 6, 2001.
STN, Registry, compound with RN 1192977-94-8, Nov. 20, 2009.
STN, Registry, RN 941951-03-7, Oct. 5, 2007.
STN, Registry, RN 949247-18-1, Oct. 5, 2007.
GNF-pf-3276 (CID 761910), URL: https://pubchem.ncbi.nlm.nih.gov/assay/assay.cgi?cid=761910.
Alonso et al., Competitive intramolecular nucleophilic aromaticsubstitution: a new route to coumarins, Chemical Communications, Issue 7, 2001, pp. 639-640.
Amaral, Therapy through chaperones: sense or antisense? Cystic fibrosis as a model disease, Journal of Inherited Metabolic Disease, vol. 29, No. 2-3, 2006, pp. 477-487.
Ameen et al., Endocytic trafficking of CFTR in health and disease, Journal of Cystic Fibrosis, vol. 6, No. 1, Jan. 2007, pp. 1-14.
Anderson et al., Chloride channels in the apical membrane of normal and cystic fibrosis airway and intestinal epithelia, American Journal of Physiology, vol. 263, No. 1, Pt 1, 1992, pp. L1-L14.
Anderson et al., Demonstration that CFTR is a chloride channel by alteration of its anion selectivity, Science, vol. 253, No. 5016, 1991, pp. 202-205.
Antunes et al., Murine nasal septa for respiratory epithelial air-liquid interface cultures, Biotechniques, vol. 43, No. 2, Aug. 2007, pp. 195-196, 198, 200 passim.
Apodaca, Endocytic traffic in polarized epithelial cells: role of the actin and microtubule cytoskeleton, Traffic, vol. 2, No. 3, Mar. 2001, pp. 149-159.
Banker et al., Modern Pharmaceutics, $3^{rd}$ edition, Marcel Dekker Inc., New York, 1996, 596 pages.
Barker et al., Effect of macrolides on in vivo ion transport across cystic fibrosis nasal epithelium, American journal of respiratory and critical care medicine, vol. 171, No. 8, Apr. 15, 2005, pp. 868-871.
Bartoszewski et al., Activation of the unfolded protein response by DeltaF508 CFTR, American Journal of Respiratory Cell and Molecular Biology, vol. 39, No. 4, Oct. 2008, pp. 448-457.
Bates et al., Membrane lateral diffusion and capture of CFTR within transient confinement zones, Biophysical Journal, vol. 91, No. 3, Aug. 1, 2006, pp. 1046-1058.
Bebok et al., Activation of Delta-F508 CFTR in an Epithelial Monolayer, American Journal of Physiology—Cell Physiology, vol. 44, No. 2 Point 1, Aug. 1998, pp. C599-C607.
Bebok et al., Failure of cAMP agonists to activate rescued deltaF508 CFTR in CFBE41o-airway epithelial monolayers, Journal of Physiology, vol. 569, Point 2, Dec. 1, 2005, pp. 601-615.
Bebok et al., The mechanism underlying CFTR transport from the endoplasmic reticulum to the proteasome includes Sec61β, and a cytosolic, deglycosylated intermediary, Journal of Biological Chemistry, vol. 273, Nov. 6, 1998, pp. 29873-29878.
Bence et al., Impairment of the ubiquitin-proteasome system by protein aggregation, Science, vol. 292, No. 5521, May 25, 2001, pp. 1552-1555.
Blad et al., Novel 3,6,7-substituted pyrazolopyrimidines as positive allosteric modulators for the hydroxycarboxylic acid receptor 2 (GPR109A), Journal of Medicinal Chemistry, vol. 55, No. 7, Apr. 12, 2012, pp. 3563-3567.
Bossard et al., NHERF1 protein rescues DeltaF508—CFTR function, American Journal of Physiology, Lung Cellular and Molecular Physiology, vol. 292, No. 5, May 2007, pp. L1085-L1094.
Boyd et al., Revisiting the mouse lung model for CF, Gene Therapy, vol. 11, No. 9, 2004, pp. 737-7387.
Bradbury et al., Biochemical and biophysical identification of cystic fibrosis transmembrane conductance regulator chloride channels as components of endocytic clathrin-coated vesicles, The Journal of Biological Chemistry, vol. 269, No. 11, Mar. 18, 1994, pp. 8296-8302.
Bubb et al., Jasplakinolide, a cytotoxic natural product, induces actin polymerization and competitively inhibits the binding of phalloidin to F-actin, The Journal of Biological Chemistry, vol. 269, No. 21, May 1994, pp. 14869-14871.
Buss et al., How are the cellular functions of myosin VI regulated within the cell?, Biochemical and Biophysical Research Communications, vol. 369, No. 1, Apr. 25, 2008, pp. 165-175.
Carlile et al., Correctors of protein trafficking defects identified by a novel high-throughput screening assay, Chembiochem—A European Journal of Chemical Biology vol. 8, No. 9, Jun. 18, 2007, pp. 1012-1020.
Chen et al., Mechanisms of cystic fibrosis transmembrane conductance regulator activation by S-nitrosoglutathione, The Journal of Biological Chemistry, vol. 281, No. 14, Apr. 7, 2006, pp. 9190-9199.

(56) References Cited

OTHER PUBLICATIONS

Cheng et al., A Golgi-associated PDZ domain protein modulates cystic fibrosis transmembrane regulator plasma membrane expression, The Journal of Biological Chemistry, vol. 277, No. 5, Feb. 1, 2002, pp. 3520-3529.

Cheng et al., Defective intracellular transport and processing of CFTR is the molecular basis of most cystic fibrosis, Cell, vol. 63, No. 4, Nov. 16, 1990, pp. 827-834.

Cheng et al., Functional activation of the cystic fibrosis trafficking mutant delta F508-CFTR by overexpression, American Journal of Physiology, vol. 268, No. 4 Point 1, Apr. 1995, pp. L615-L624.

Choi et al., Synergistic airway gland mucus secretion in response to vasoactive intestinal peptide and carbachol is lost in cystic fibrosis, The Journal of Clinical Investigation, vol. 117, No. 10, Oct. 2007, pp. 3118-3127.

Chou et al., Ziram causes dopaminergic cell damage by inhibiting E1 ligase of the proteasome, The Journal of Biological Chemistry, vol. 283, No. 50, Dec. 12, 2008, pp. 34696-34703.

Clancy et al., No detectable improvements in cystic fibrosis transmembrane conductance regulator by nasal aminoglycosides in patients with cystic fibrosis with stop mutations, American Journal of Respiratory Cell and Molecular Biology, vol. 37, No. 1, Jul. 2007, pp. 57-66.

Clarke et al., A domain mimic increases DeltaF508 CFTR trafficking and restores cAMP-stimulated anion secretion in cystic fibrosis epithelia, American Journal of Physiology. Cell Physiology, vol. 287, No. 1, Jul. 2004, pp. C192-C199.

Cotlin et al., Casein Kinase II activity is required for transferrin receptor endocytosis, Journal of Biological Chemistry, vol. 274, No. 43, Oct. 1999, pp. 30550-30556.

Coux et al., Structure and functions of the 20S and 26S proteasomes, Annual Review of Biochemistry, vol. 65, 1996, pp. 801-847.

Cushing et al., The relative binding affinities of PDZ partners for CFTR: a biochemical basis for efficient endocytic recycling, Biochemistry, vol. 47, No. 38, 2008, pp. 10084-10098.

Davidson et al., Mouse models of cystic fibrosis, Trends in Genetics, vol. 17, No. 10, Oct. 2001, pp. S29-S37.

Davidson et al., The CF mouse: An Important Tool for Studying Cystic Fibrosis, Expert Reviews in Molecular Medicine, vol. 2001, Mar. 2001, pp. 1-27.

Denning et al., Processing of mutant cystic fibrosis transmembrane conductance regulator is temperature-sensitive, Nature, vol. 358, No. 6389, 1992, pp. 761-764.

Desai et al., A convenient, rapid and eco-friendly synthesis of isoxazoline heterocyclic moiety containing bridge at 2°-amine as potential pharmacological agent, Journal of the Iranian Chemical Society, vol. 5, Issue 1, [online] CAS (STN), 150:237474, RN 1115854-28-8, RM 1115854-38-0, RN 1115854-41-5, RN 1115854-40-4, Mar. 2008, pp. 67-73.

Didenko et al., Regioselective and Regiospecific Reactions of Ethyl ortho-(Dimethylaminovinylazoloazinylcarboxylates with Hydrazine, Russian J. of General Chem., vol. 80, No. 4, 2010, pp. 814-817.

Didenko et al., Synthesis of 7,8-Dihydro-6H-Pyrazolo[5', 1':3,4][1,2,4]-Triazino[6,5-d][1,2] Diazepin-6-one, a New Heterocyclic System, Chemistry of Heterocyclic Compounds, 2009, pp. 248-249.

Drabczynska et al., N9-Benzyl-substituted 1,3-dimethyl- and 1,3-dipropyl-pyrimido[2, 1-f]purinediones: Synthesis and structure-activity relationships at adenosine A1 and A2A receptors, Bioorganic & Medicinal Chemistry, vol. 15, 2007, pp. 5003-5017.

Eden et al., Adaptor protein disabled-2 modulates low density lipoprotein receptor synthesis in fibroblasts from patients with autosomal recessive hypercholesterolaemia, Human Molecular Genetics, vol. 16, No. 22, Nov. 15, 2007, pp. 2751-2759.

Elnagdi et al., Reactions with heterocyclic amidines, VII: Synthesis of some new pyrazolo[1,5-c]-1,2,4-triazines, pyrazolo[1,5-a]-1,3,5-triazines and pyrazolo[1,5-a]pyrimidines, Monatshefte für Chemie, vol. 112, 1981, pp. 245-252.

Estell et al., Plasma membrane CFTR regulates RANTES expression via its C-terminal PDZ-interacting motif, Molecular and Cellular Biology, vol. 23, No. 2, Jan. 2003, pp. 594-606.

Gentzsch et al., Endocytic trafficking routes of wild type and DeltaF508 cystic fibrosis transmembrane conductance regulator, Molecular biology of the cell, vol. 15, No. 6, Jun. 2004, pp. 2684-2696.

Gilon et al., Degradation signals for ubiquitin system proteolysis in *Saccharomyces cerevisiae*, EMBO Journal, vol. 17, No. 10, 1998, pp. 2759-2766.

Goldstein et al., VCP/p97 AAA-ATPase Does Not Interact with the Endogenous Wild-Type Cystic Fibrosis Transmembrane Conductance Regulator, American Journal of Respiratory Cell and Molecular Biology, vol. 36, No. 6, Jun. 2007, pp. 706-714.

Gonda, The ascent of pulmonary drug delivery, Journal of Pharmaceutical Sciences, vol. 89, Issue 7, Jul. 2000, pp. 940-945.

Gregg et al., Pyrazolo[1,5-a]pyrimidines. Identification of the privileged structure and combinatorial synthesis of 3-(hetero)arylpyrazolo[1,5-a]pyrimidine-6-carboxamides, J. Comb. Chem., vol. 9, Issue 3, May-Jun. 2007, pp. 507-512.

Grubb et al., Pathophysiology of gene-targeted mouse models for cystic fibrosis, Physiological Reviews, vol. 79, Supplementary 1, Jan. 1999, pp. S193-S214.

Guggino et al., Macromolecular interactions and ion transport in cystic fibrosis, American journal of respiratory and critical care medicine, vol. 170, No. 7, 2004, pp. 815-820.

Guggino et al., New insights into cystic fibrosis: molecular switches that regulate CFTR, Nature Reviews. Molecular Cell Biology, vol. 7, No. 6, Jun. 2006, pp. 426-436.

Haggie et al., Tracking of quantum dot-labeled CFTR shows near immobilization by C-terminal PDZ interactions, Molecular biology of the cell, vol. 17, No. 12, Dec. 2006, pp. 4937-4945.

Hanmantgad et al., Biomimetic thiazolyl coumarins. National Academy, Science Letters, vol. 7, Issue 3, CAS (STN), 103:53986, compound of the formula I, RN: 97268-10-5, 1984, pp. 77-78.

Hardtmann et al., Synthesis and Biological Evaluation of Some 1 a-Substituted 2,3-Dihydroirnidazo[2, 1- b]quinazolin-5 ( 1 OH)-ones, a New Class of Bronchodilatorst, May 1, 1975, pp. 447-453.

Heasman et al., Mammalian Rho GTPases: new insights into their functions from in vivo studies, Nature Reviews—Molecular Cell Biology, vol. 9, No. 9, Sep. 2008, pp. 690-701.

Heda et al., The ΔF508 mutation shortens the biochemical half-life of plasma membrane CFTR in polarized epithelial cells, American Journal of Physiology—Cell Physiology, vol. 280, Jan. 1, 2001, pp. C166-C174.

Hunter et al., Ubiquitin-proteasome system alterations in a striatal cell model of huntington's disease, Journal of Neuroscience Research, vol. 85, No. 8, Jun. 2007, pp. 1774-1788.

Hyde et al., Structural model of ATP-binding proteins associated with cystic fibrosis, multidrug resistance and bacterial transport, Nature, vol. 346, No. 6282, Jul. 26, 1990, pp. 362-365.

Ianowski et al., Mucus secretion by single tracheal submucosal glands from normal and cystic fibrosis transmembrane conductance regulator knockout mice, Journal of Physiology, vol. 580, Point 1, Apr. 1, 2007, pp. 301-314.

Ishikura et al., Small G proteins in insulin action: Rab and Rho families at the crossroads of signal transduction and GLUT4 vesicle traffic, Acta Physiologica, vol. 192, No. 1, 2008, pp. 61-74.

Jensen et al., Multiple proteolytic systems, including the proteasome, contribute to CFTR processing, Cell, vol. 83, No. 1, Oct. 6, 1995, pp. 129-135.

Jin et al., Single-particle tracking of membrane protein diffusion in a potential: simulation, detection, and application to confined diffusion of CFTR Cl-channels, Biophysical Journal, vol. 93, No. 3, Aug. 1, 2007, pp. 1079-1088.

Jurkuvenaite et al., Mutations in the Amino Terminus of the Cystic Fibrosis Transmembrane Conductance Regulator Enhance Endocytosis, The Journal of Biological Chemistry, vol. 281, No. 6, Feb. 2006, pp. 3329-3334.

Kirk, New paradigms of CFTR chloride channel regulation, Cellular and Molecular Life Sciences, vol. 57, No. 4, 2000, pp. 623-634.

(56) References Cited

OTHER PUBLICATIONS

Knowles et al., Abnormal ion permeation through cystic fibrosis respiratory epithelium, Science, vol. 221, No. 4615, Sep. 9, 1983, pp. 1067-1070.
Koller et al., Toward an animal model of cystic fibrosis: targeted interruption of exon 10 of the cystic fibrosis transmembrane regulator gene in embryonic stem cells, PNAS, vol. 88, No. 23, Dec. 1991, pp. 10730-10734.
Korzycka, Synthesis and pharmacological investigations of new 6-oxo-1,2,3,4-tetrahydro-6H-pyrimido[2,1- b]quinazoline derivatives, Pharmazie, vol. 49, Issue 11, Nov. 1994, pp. 815-819.
Kowanetz et al., Dab2 links CIN85 with clathrin-mediated receptor internalization, FEBS Letters, vol. 554, No. 1-2, Nov. 2003, pp. 81-87.
Kowanetz et al., Identification of a novel proline-arginine motif involved in CIN85-dependent clustering of Cbl and down-regulation of epidermal growth factor receptors, The Journal of Biological Chemistry, vol. 278, No. 41, Oct. 2003, pp. 39735-39746.
Kozhushko et al., 2-(o-Carboxyphenylamino)-6-Hpyrimido[ 2, 1-13]quinazol-6-one ester hydrochlorides with antiinflammatory, analgesic, and antipyretic activity, Chemical Abstracts Service, Jul. 15. 1987.
Kunzelmann et al., An immortalized cystic fibrosis tracheal epithelial cell line homozygous for the delta F508 CFTR mutation, American Journal of Respiratory Cell and Molecular Biology, vol. 8, No. 5, 1993, pp. 522-529.
Kwon et al., Knockdown of NHERF1 enhances degradation of temperature rescued DeltaF508 CFTR from the cell surface of human airway cells, Cellular Physiology and Biochemistry, vol. 20, No. 6, Feb. 2007, pp. 763-772.
Lack et al., Targeting the Binding Function 3 (BF3) Site of the Human Androgen Receptor through Virtual Screening, Journal of Medicinal Chemistry, vol. 54, No. 24, Dec. 22, 2011, pp. 8563-8573.
Laddha et al., A new therapeutic approach in Parkinson's disease: Some novel quinazoline derivatives as dual selective phosphodiesterase 1 inhibitors and anti-inflammatory agents, Bioorganic & Medicinal Chemistry, Pergamon, GB, vol. 17, No. 19, Oct. 1, 2009, pp. 6796-6802.
Lechner et al., A serum-free method for culturing. normal human epithelial cells at clonal density, Journal of Tissue Culture Methods, vol. 9, No. 2, 1985, pp. 43-48.
Leung, Modulation of endocytic traffic in polarized Madin-Darby canine kidney cells by the small GTPase RhoA, Molecular biology of the cell, vol. 10, No. 12, Dec. 1999, pp. 4369-4384.
Logan et al., Cationic lipids for reporter gene and CFTR transfer to rat pulmonary epithelium, Gene Therapy, vol. 2, No. 1, Jan. 1995, pp. 38-49.
Lukacs et al., Conformational maturation of CFTR but not its mutant counterpart (delta F508) occurs in the endoplasmic reticulum and requires ATP, EMBO Journal, vol. 13, No. 24, Dec. 1994, pp. 6076-6086.
Lukacs et al., Constitutive internalization of cystic fibrosis transmembrane conductance regulator occurs via clathrin-dependent endocytosis and is regulated by protein phosphorylation, The Biochemical journal, vol. 328, Point 2, Dec. 1997, pp. 353-361.
Matsui et al., Evidence for periciliary liquid layer depletion, not abnormal ion composition, in the pathogenesis of cystic fibrosis airways disease, Cell, vol. 95, No. 7, Dec. 23, 1998, pp. 1005-1015.
Mazzochi et al., Interaction of epithelial ion channels with the actinbased cytoskeleton, American Journal of Physiology—Renal Physiology, vol. 291, No. 6, Dec. 2006, pp. F1113-F1122.
Meacham et al., The Hsc70 co-chaperone CHIP targets immature CFTR for proteasomal degradation, Nature Cell Biology, vol. 3, No. 1, Jan. 2001, pp. 100-105.
Mitra et al., RNAi-based analysis of CAP, Cbl, and Crkll function in the regulation of GLUT4 by insulin, The Journal of Biological Chemistry, vol. 279, No. 36, Sep. 3, 2004, pp. 37431-37435.

Mori et al., A Combination Strategy to Inhibit Pim-1: Synergism between Noncompetitive and ATP-Competitive Inhibitors, ChemMedChem., vol. 8, Issue 3, Feb. 22, 2013, pp. 484-496.
Morris et al., Myosin VI binds to and localises with Dab2, potentially linking receptor-mediated endocytosis and the actin cytoskeleton, Traffic, vol. 3, No. 5, May 2002, pp. 331-341.
Naren et al., A macromolecular complex of beta 2 adrenergic receptor, CFTR, and ezrin/radixin/moesin-binding phosphoprotein 50 is regulated by PKA, PNAS, vol. 100, No. 1, Jan. 7, 2003, pp. 342-346.
NCBI, CID 16417802, PubChem Compound, Jul. 31, 2007.
NCBI, CID 2806960, ZINC00145317, PubChem Compound, Open Chemistry Database, Jul. 19, 2005.
Okiyoneda , Cell surface dynamics of CFTR: the ins and outs, Biochimica et Biophysica Acta (BBA)—Molecular Cell Research, vol. 1773, No. 4, Apr. 2007, pp. 476-479.
Panigrahi et al., 4-(3'-Coumarinyl)-2-arylaminothiazoles and some of their derivatives, Journal of the Indian Chemical Society, vol. 48, Issue 7, [online] CAS (STN), 75:129705, RN 33856-02-9, RN 33856-03-0, RN 33856-04-1, RN 33856-05-2, RN 33856-06-3, RN 33856-07-4, RN 34560-08-2., 1971, pp. 665-668.
Pastva et al., Aerobic exercise attenuates airway inflammatory responses in a mouse model of atopic asthma, Journal of Immunology, vol. 172, No. 7, Apr. 2004, pp. 4520-4526.
Pastva et al., RU486 blocks the anti-inflammatory effects of exercise in a murine model of allergen-induced pulmonary inflammation, Brain, Behavior, and Immunity, vol. 19, No. 5, Sep. 2005, pp. 413-422.
Peter et al., Ablation of internalization signals in the carboxyl-terminal tail of the cystic fibrosis transmembrane conductance regulator enhances cell surface expression, The Journal of Biological Chemistry, vol. 277, No. 51, Dec. 20, 2002, pp. 49952-49957.
Picciano et al., Rme-1 regulates the recycling of the cystic fibrosis transmembrane conductance regulator, American Journal of Physiology—Cell Physiology, vol. 285, 2003, pp. C1009-C1018.
Prince et al., Efficient endocytosis of the cystic fibrosis transmembrane conductance regulator requires a tyrosine-based signal, Journal of Biological Chemistry, vol. 274, No. 6, Feb. 5, 1999, pp. 3602-3609.
Prince et al., Rapid endocytosis of the cystic fibrosis transmembrane conductance regulator chloride channel, PNAS, vol. 91, No. 11, May 24, 1994, pp. 5192-5196.
Rab et al., Endoplasmic Reticulum Stress and the Unfolded Protein Response Regulate Genomic Cystic Fibrosis Transmembrane Conductance Regulator Expression, American Journal of Physiology—Cell Physiology, vol. 292, No. 2, Feb. 2006, pp. C756-C766.
Rao et al., The Cbl family of ubiquitin ligases: critical negative regulators of tyrosine kinase signaling in the immune system, Journal of Leukocyte Biology, vol. 71, No. 5, May 2002, pp. 753-763.
Ratjen et al., Cystic Fibrosis, Lancet, vol. 361, No. 9358, Feb. 2003, pp. 681-689.
Riordan et al., Identification of the cystic fibrosis gene: cloning and characterization of complementary DMA, [published erratum appears in Science Sep. 29, 1989; 245(4925)1 437]. Science, vol. 245, 1989, pp. 1066-1073.
Robelet et al., Pharmacological effects of some 8-substituted theophylline derivatives, Journal de Physiologie, vol. 57, 1965, pp. 689-690.
Romanenko et al., Synthesis and physicochemical properties of 1-methyl-6, 7 ,8,9-tetrahydropyrimido[2, 1-f]xanthine derivatives, Ukrainskii Khimicheskii Zhurnal, vol. 60, 1994, pp. 300-302.
Romanenko et al., The synthesis and pharmacological activity of the derivatives of 1-methyl-3H-6,9-dihydro-1 ,2,4-triazino[3,44]xanthine, KhimicoFarmatsevticheskii Zhurnal, vol. 20, 1986, pp. 187-190.
Rubenstein et al., Clinical trials of 4-phenylbutyrate for correction of sweet duct abnormalities in DF508 homozygous cystic fibrosis patients, Pediatric Pulmonary, Supplementary 13, 1996, p. 259.
Salaheldin et al., Studies with enaminonitriles: Synthesis and chemical reactivity of 2-phenyl-3-piperidin-1-yl acrylonitrile under microwave heating, Journal of Heterocyclic Chemistry, vol. 45, Issue 2, Mar./Apr. 2008, pp. 307-310.

(56) References Cited

OTHER PUBLICATIONS

Samura, Effect of imidazo(1,2-f)xanthine derivatives on cerebral cortical bioelectrical activity and evoked potentials, Farmakol Toksikol, vol. 46, issue 1, Feb. 28, 1983, pp. 17-20.
Sato et al., Glycerol reverses the misfolding phenotype of the most common cystic fibrosis mutation, Journal of Biological Chemistry, vol. 271, No. 2, Jan. 12, 1996, pp. 635-638.
Schroder et al., ER stress and the unfolded protein response, Mutation Research, vol. 569, Jan. 26, 2005, pp. 29-63.
Schroder et al., The Mammalian Unfolded Protein Response, Annual Review of Biochemistry, vol. 74, 2005, pp. 739-789.
Schultz et al., Pharmacology of CFTR chloride channel activity, Physiological Reviews, vol. 79, No. 1, Jan. 1999, pp. S109-S144.
Schwiebert et al., CFTR is a conductance regulator as well as a chloride channel, Physiological Reviews, vol. 79, 1999, pp. S145-S166.
Sharma et al., Conformational and temperature-sensitive stability defects of the DF508 cystic fibrosis transmembrane conductance regulator in post-endoplasmic reticulum compartments, Journal of Biological Chemistry, vol. 276, 2001, pp. 8942-8950.
Sharma et al., Misfolding diverts CFTR from recycling to degradation: quality control at early endosomes, Journal of Cell Biology, vol. 164, No. 6, Mar. 15, 2004, pp. 923-933.
Shen et al., Discovery of pyrazolopyrimidines as the first class of allosteric agonists for the high affinity nicotinic acid receptor GPR109A, Bioorganic & Medical Chemistry Letters, vol. 18, No. 18, Sep. 15, 2008, pp. 4948-4951.
Short et al., An apical PDZ protein anchors the cystic fibrosis transmembrane conductance regulator to the cytoskeleton, The Journal of Biological Chemistry, vol. 273, No. 31, Jul. 31, 1998, pp. 19797-19801.
Shumay et al., Lysophosphatidic acid regulates trafficking of beta 2-adrenergic receptors:the Galpha 13/p115RHOGEF/JNK pathway stimulates receptor internalization, Journal of Biological Chemistry, vol. 282, No. 29, 2007, pp. 21529-21541.
Snouwaert et al., An animal model for cystic fibrosis made by gene targeting, Science, vol. 257, No. 5073, Aug. 21, 1992, pp. 1083-1088.
Sorscher et al., Gene therapy for cystic fibrosis using cationic liposome mediated gene transfer: a phase I trial of safety and efficacy in the nasal airway, Human Gene Therapy, vol. 5, No. 10, Oct. 1994, pp. 1259-1277.
Soubeyran et al., Cbl-CIN85-endophilin complex mediates ligand-induced downregulation of EGF receptors, Nature, vol. 416, No. 6877, Mar. 14, 2002, pp. 183-187.
Spector et al., Latrunculins: novel marine toxins that disrupt microfilament organization in cultured cells, Science, vol. 219, No. 4584, Feb. 4, 1983, pp. 493-495.
Srimanth et al., Synthesis of some new types ofthiazolyl coumarins, Indian Journal of Chemistry, vol. 388, No. 4, [online] CAS (STN), 131:228681, RN 244104-97-0., 1999, pp. 473-475.
Swiatecka-Urban et al., Myosin Vb is required for trafficking of the cystic fibrosis transmembrane conductance regulator in Rab11a-specific apical recycling endosomes in polarized human airway epithelial cells, The Journal of Biological Chemistry, vol. 282, Aug. 10, 2007, pp. 23725-23736.
Swiatecka-Urban et al., Myosin VI regulates endocytosis of the cystic fibrosis transmembrane conductance regulator, The Journal of Biological Chemistry, vol. 279, Sep. 3, 2004, pp. 38025-38031.
Swiatecka-Urban et al., PDZ domain interaction controls the endocytic recycling of the cystic fibrosis transmembrane conductance regulator, Journal of Biological Chemistry, vol. 277, No. 42, Oct. 18, 2002, pp. 40099-40105.
Swiatecka-Urban et al., The short apical membrane half-life of rescued {Delta}F508-cystic fibrosis transmembrane conductance regulator (CFTR) results from accelerated endocytosis of {Delta}F508-CFTR in polarized human airway epithelial cells, The Journal of Biological Chemistry, vol. 280, No. 44, Nov. 4, 2005, pp. 36762-36772.
Symons et al., Control of vesicular trafficking by Rho GTPases, Current Biology, vol. 13, No. 10, May 13, 2003, pp. R409-R418.
Tarran et al., Regulation of murine airway surface liquid volume by CFTR and Ca2+-activated Clconductances, Journal of General Physiology, vol. 120, No. 3, Sep. 2002, pp. 407-418.
Tarran et al., Soluble mediators, not cilia, determine airway surface liquid volume in normal and cystic fibrosis superficial airway epithelia, Journal of General Physiology, vol. 127, No. 5, May 2006, pp. 591-604.
Touitou, A degradation signal located in the C-terminus of p21WAF1/CIP1 is a binding site for the C8 alpha-subunit of the 20S proteasome, EMBO Journal, vol. 20, No. 10, May 15, 2001, pp. 2367-2375.
Tripathi et al., CHIP chaperones wild type p53 tumor suppressor protein, The Journal of Biological Chemistry, vol. 282, No. 39, Sep. 28, 2007, pp. 28441-28454.
Tripathi et al., Cullin4B/E3-ubiquitin ligase negatively regulates betacatenin, Journal of Biosciences, vol. 32, No. 6, Sep. 2007, pp. 1133-1138.
Tucker et al., Transient transfection of polarized epithelial monolayers with CFTR and reporter genes using efficacious lipids, American Journal of Physiology, Cell Physiology, vol. 284, 2003, pp. C791-C804.
Van Ginkel et al., Adenoviral gene delivery elicits distinct pulmonary-associated T helper cell responses to the vector and to its transgene, Journal of Immunology, vol. 159, No. 2, Jul. 15, 1997, pp. 685-693.
Van Goor et al., Rescue of deltaF508-CFTR Function by Small Molecules in Human Bronchial Epithelial Isolated from CF Patients, Pediatric Pulmonology, vol. 38, 2004, p. 247.
Van Goor et al., Rescue of DeltaF508-CFTR trafficking and gating in human cystic fibrosis airway primary cultures by small molecules, American Journal of Physiology. lung cellular and molecular physiology vol. 290, No. 6, Jun. 1, 2006, pp. L1117-L1130.
Varga et al., Efficient intracellular processing of the endogenous cystic fibrosis transmembrane conductance regulator in epithelial cell lines, The Journal of Biological Chemistry, vol. 279, No. 21, May 21, 2004, pp. 22578-22584.
Varga et al., Enhanced cell-surface stability of rescued DeltaF508 cystic fibrosis transmembrane conductance regulator (CFTR) by pharmacological chaperones, The Biochemical journal, vol. 410, No. 3, Mar. 15, 2008, pp. 555-564.
Venugopala et al., Synthesis and evaluation of some substituted 2-arylamino coumarinyl thiazoles as potential NSAIDs, Asian Journal of Chemistry, vol. 16, No. 2, [online] CAS (STN), 142:219187, RN 33856-02-9, RN 33856-03-0, RN 33856-04-1, RN 33856-06-3, RN 97268-08-1, RN 97268-09-2, RN 313668-62-1, RN 325805-75-2, RN 33856-02-9, 2004, pp. 872-876.
Vij et al., Selective inhibition of endoplasmic reticulum-associated degradation rescues DeltaF508-cystic fibrosis transmembrane regulator and suppresses interleukin-8 levels: therapeutic implications, The Journal of Biological Chemistry, vol. 281, No. 25, Jun. 23, 2006, pp. 17369-17378.
Wang et al., Chemical and biological folding contribute to temperature-sensitive DeltaF508 CFTR trafficking, Traffic, vol. 9, No. 11, Nov. 2008, pp. 1878-1893.
Wang et al., Hsp90 cochaperone Aha1 downregulation rescues misfolding of CFTR in cystic fibrosis, Cell, vol. 127, No. 4, Nov. 17, 2006, pp. 803-815.
Wang et al., Reversible silencing of CFTR chloride channels by glutathionylation, Journal of General Physiology, vol. 125, No. 2, Feb. 2005, pp. 127-141.
Ward et al., Degradation of CFTR by the ubiquitin-proteasome pathway, Cell, vol. 83, No. 1, Oct. 6, 1995, pp. 121-127.
Weixel et al., Endocytic adaptor complexes bind the C-terminal domain of CFTR, Pflügers Archiv—European Journal of Physiology, vol. 443, Issue 1, Feb. 2001, pp. S70-S74.
Weixel et al., Mu 2 binding directs the cystic fibrosis transmembrane conductance regulator to the clathrin-mediated endocytic pathway, The Journal of Biological Chemistry, vol. 276, No. 49, Dec. 7, 2001, pp. 46251-46259.
Wilschanski et al., A pilot study of the effect of gentamicin on nasal potential difference measurements in cystic fibrosis patients carry-

(56) References Cited

OTHER PUBLICATIONS ing stop mutations, American journal of respiratory and critical care medicine, vol. 161, No. 3, Point 1, Mar. 2000, pp. 860-865.

Wilschanski et al., Gentamicin-induced correction of CFTR function in patients with cystic fibrosis and CFTR stop mutations, The New England Journal of Medicine, vol. 349, No. 15, Oct. 9, 2003, pp. 1433-1441.

Wolde et al., Targeting CAL as a negative regulator of DeltaF508-CFTR cell-surface expression: an RNA interference and structure-based mutagenetic approach, The Journal of Biological Chemistry, vol. 282, No. 11, Mar. 16, 2007, pp. 8099-8109.

Wolff, Burger's Medicinal Chemistry and Drug Discovery, Principles and Practice, John Wiley & Sons, Fifth edition, vol. 1, 1995, p. 975.

Woodworth et al., Murine tracheal and nasal septal epithelium for air-liquid interface cultures: a comparative study, American Journal of Rhinology, vol. 21, No. 5, Sep./Oct. 2007, pp. 533-537.

Xu et al., Identification of natural coumarin compounds that rescue defective DeltaF508-CFTR chloride channel gating, Clinical and Experimental Pharmacology and Physiology, vol. 35, Issue 8, Aug. 2008, pp. 878-883.

Yang et al., Inhibitors of ubiquitin-activating enzyme (E1), a new class of potential cancer therapeutics, Cancer Research, vol. 67, No. 19, Oct. 1, 2007, pp. 9472-9481.

Yang et al., Stimulation of Airway and Intestinal Mucosal Secretion by Natural Coumarin CFTR Activators, Frontiers in Pharmacology, vol. 2, Issue 52, Sep. 27, 2011, 5 pages.

Yoneda et al., Synthesis ofxanthines by dehydrogenative cyclization of6-amino-5-benzylideneaminouracils with diethyl azodicarboxylate, Chemical & Pharmaceutical Bulletin, vol. 26, issue 9 p, 1978, pp. 2905-2910.

Zeiher et al., A mouse model for the delta F508 allele of cystic fibrosis, The Journal of Clinical Investigation, vol. 96, No. 4, Oct. 1995, pp. 2051-2064.

Zhou et al., Nedd4-2 catalyzes ubiquitination and degradation of cell surface ENaC, The Journal of Biological Chemistry, vol. 282, No. 28, Jul. 13, 2007, pp. 20207-20212.

Zsembery et al., Extracellular zinc and ATP restore chloride secretion across cystic fibrosis airway epithelia by triggering calcium entry, Journal of Biological Chemistry, vol. 279, No. 11, Mar. 12, 2004, pp. 10720-10729.

European Application No. 12785637.5, Extended European Search Report mailed on Mar. 30, 2015, 17 pages.

European Application No. 12785637.5, Partial Supplementary European Search Report, Dec. 12, 2014, 10 pages.

International Application No. PCT/US2012/038347, International Preliminary Report on Patentability mailed on Nov. 28, 2013, 10 pages.

International Application No. PCT/US2012/038347, International Search Report and Written Opinion mailed on Nov. 28, 2012, 14 pages.

International Application No. PCT/US2013/070987, International Preliminary Report on Patentability mailed on Jun. 4, 2015, 8 pages.

International Application No. PCT/US2013/070987, International Search Report and Written Opinion mailed on Apr. 17, 2014, 11 pages.

U.S. Appl. No. 14/117,705, Ex Parte Quayle Action mailed on May 27, 2015, 4 pages.

U.S. Appl. No. 14/117,705, Non-Final Office Action mailed on Dec. 15, 2014, 11 pages.

U.S. Appl. No. 14/117,705, Notice of Allowance mailed on Jul. 7, 2015, 7 pages.

U.S. Appl. No. 14/117,705, Restriction Requirement mailed on Aug. 15, 2014, 12 pages.

U.S. Appl. No. 14/646,092, "Non-Final Office Action", May 11, 2016, 19 pages.

Blad, et al., "Novel 3,6,7-Substituted Pyrazolopyrimidines as Positive Allosteric Modulators for the Hydroxycarboxylic Acid Receptor 2 (GPR109A)", Journal of Medicinal Chemistry, vol. 55, No. 7, Apr. 12, 2012, pp. 3563-3567.

Database Registry [Online] Chemical Abstracts Service, Database accession No. 1204298-07-6, Feb. 1, 2010.

Database Registry [Online] Chemical Abstracts Service, Database accession No. 1030421-22-7, Jun. 24, 2008.

Didenko, et al., "Synthesis of 7 ,8-Dihydro-6H-Pyrazolo[,1' :3,41 ] [1,2,4]Triazino[ 6,5-d] [1,2] Diazepin-6-One. A New Heterocyclic System", Chemistry of Heterocyclic Compounds, vol. 45, Feb. 1, 2009, pp. 307-308.

Drabczynska, et al., "Synthesis and biological activity of tricyclic cycloalkylimidazo-, pyrimido- and diazepinopurinediones", Eur. J. of Med. Chem. 46(9), 2011, pp. 3590-3607.

Ege, et al., "Cycloaddition von Ynaminen an Diazo-azole. Ein neuer Zugang zu Azolo [5,1-c][1,2,4]triazinen", Synthesis, Aug. 1, 1977, pp. 556-559.

EP13 857 342.3, "Extended European Search Report", Apr. 28, 2016, 12 pages.

Kheder, "Convenient Synthesis of Novel Bis(hydrazone) and Bis(indole) Derivatives", Heterocycles, vol. 78, No. 5, Jan. 14, 2009, pp. 1281-1288.

Padwa, et al., "Extended dipolar cycloaddition reactions of 3-diazopyrazoles with electron rich olefins", Tetrahedron Letters, vol. 22, No. 13, Jan. 1, 1981, pp. 1199-1202.

Zagorska, et al., "Serotonin transporter activity of imidazolidine-2,4-dione and imidazo[2,1-f]purine-2,4-dione derivatives in aspect of their acid-base properties", Med. Chem. Res., 21(11), 2012, pp. 3455-3459.

Zayed, et al., "Synthesis of some new fused azoles from pyrazolo[1,5-c]-as-triazine derivative", Pharmazie, vol. 39, No. 6, 1984, pp. 432-433.

\* cited by examiner

SMALL MOLECULE CFTR CORRECTORS

CROSS-REFERENCE TO PRIORITY APPLICATION

This application claims priority to U.S. Provisional Application No. 61/728,414, filed Nov. 20, 2012, which is incorporated herein by reference in its entirety.

STATEMENT REGARDING FEDERALLY FUNDED RESEARCH

This invention was made with government support under Grant No. NIDDK Phase II SBIR DK084658-03 awarded by the National Institutes of Health. The government has certain rights in the invention.

BACKGROUND

Cystic fibrosis is an example of a protein folding disorder. It is a hereditary disease caused by mutations in a gene encoding the cystic fibrosis transmembrane conductance regulator (CFTR). The CFTR gene encodes a chloride channel that is expressed in multiple epithelial cell types. A common CFTR mutation, delF508, causes the failure of CFTR to traffic correctly to the plasma membrane because of protein misfolding. The delF508 mutation is estimated to account for 90% of mutant alleles. Because of its high degree of incidence in the cystic fibrosis population, delF508-CFTR is a prime target for cystic fibrosis therapeutics. As such, delF508-CFTR has been extensively studied and is a model for the study of protein folding diseases.

SUMMARY

Compounds and methods for the treatment of protein folding disorders are provided. Cystic fibrosis (CF) is used throughout as an example of such a protein folding disorder. The methods include administering to a subject a CFTR corrector (i.e., a compound effective in rescuing halide efflux in a cell).

A class of CFTR correctors includes compounds of the following formula:

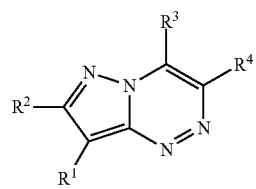

or pharmaceutically acceptable salts or prodrugs thereof. In this class of compounds, $R^1$ is substituted or unsubstituted alkyl, substituted or unsubstituted cycloalkyl, or substituted or unsubstituted aryl; $R^2$ is hydrogen, substituted or unsubstituted alkyl, or substituted or unsubstituted aryl; $R^3$ is hydrogen, substituted or unsubstituted alkyl, substituted or unsubstituted amino, or substituted carbonyl; and $R^4$ is substituted or unsubstituted alkyl, substituted carbonyl, substituted or unsubstituted heteroaryl, or substituted or unsubstituted amino. Optionally, the compound has the following structure:

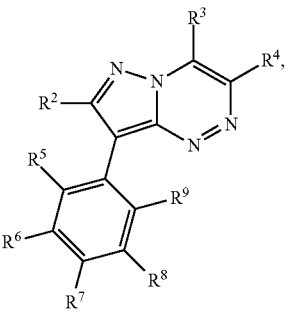

wherein $R^5$, $R^6$, $R^7$, $R^8$, and $R^9$ are each independently selected from the group consisting of hydrogen, halogen, hydroxyl, and substituted or unsubstituted alkoxy. Optionally, the compound has the following structure:

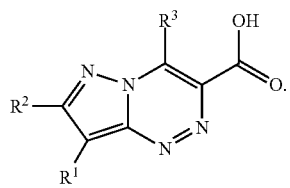

Optionally, the compound has the following structure:

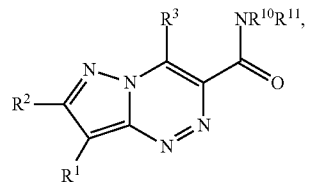

wherein $R^{10}$ and $R^{11}$ are each independently selected from the group consisting of hydrogen and substituted or unsubstituted alkyl. Optionally, the compound has the following structure:

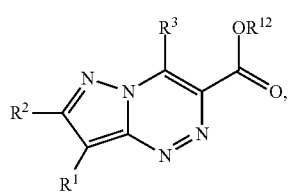

wherein $R^{12}$ is hydrogen, substituted or unsubstituted alkyl, or substituted or unsubstituted cycloalkyl. Optionally, the compound is selected from the group consisting of:

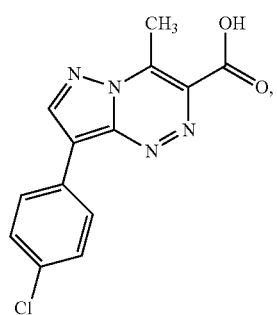

3
-continued

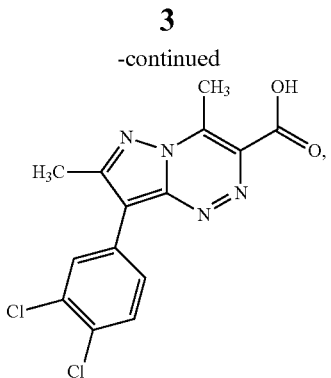

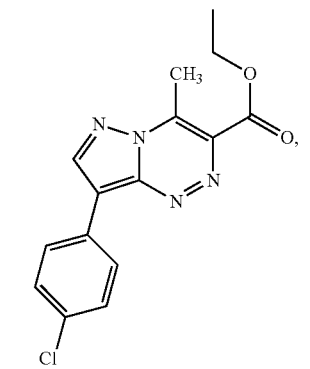

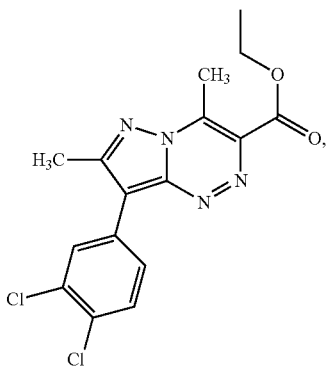

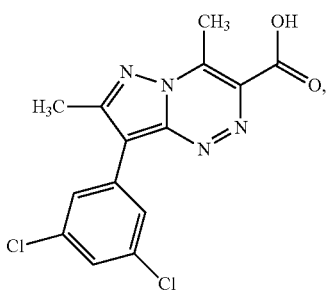

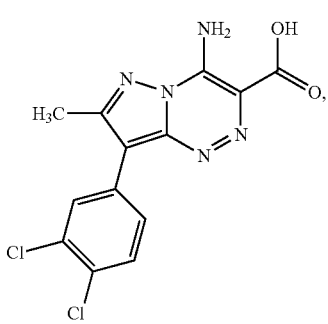 [SMILES: Cc1nn2c(C)c(C(=O)O)cnc2c1-c1ccc(Cl)c(Cl)c1]

4
-continued

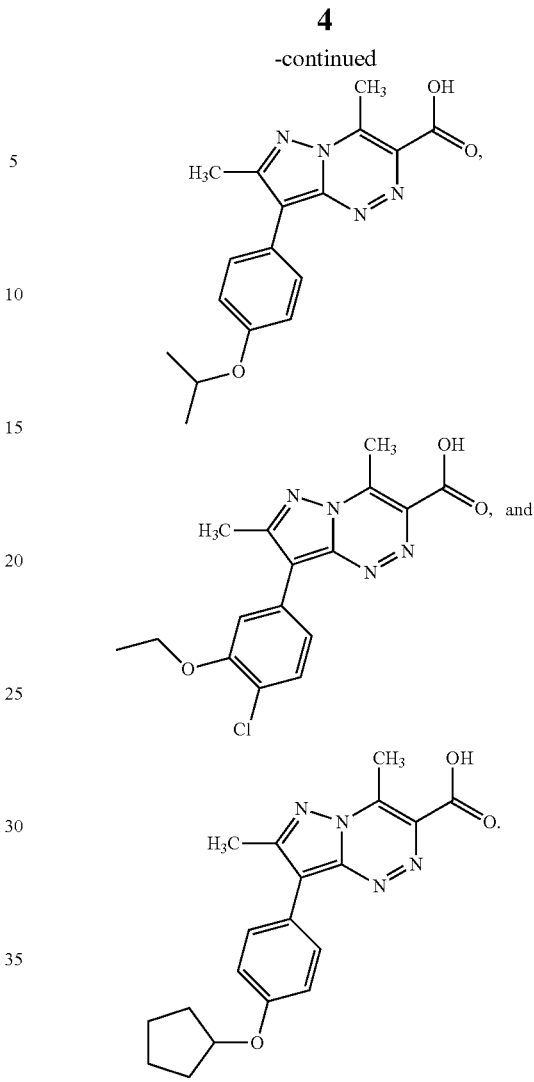

A class of CFTR correctors includes compounds of the following structure:

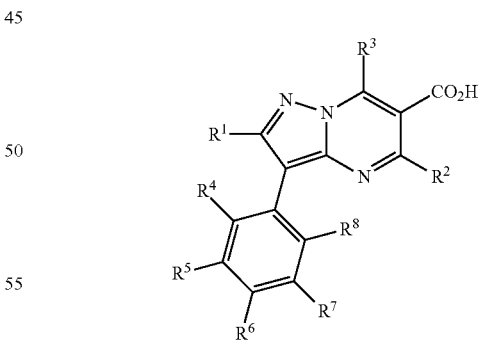

or pharmaceutically acceptable salts or prodrugs thereof. In this class of compounds, $R^1$, $R^2$, and $R^3$ are each independently selected from the group consisting of hydrogen and substituted or unsubstituted alkyl; and $R^4$, $R^5$, $R^6$, $R^7$, and $R^8$ are each independently selected from the group consisting of hydrogen, halogen, hydroxyl, substituted or unsubstituted alkyl, and substituted or unsubstituted aryl. Optionally, the compound is

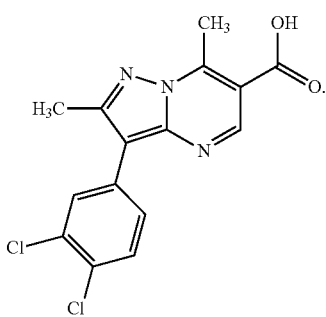

A class of CFTR correctors includes compounds of the following formula:

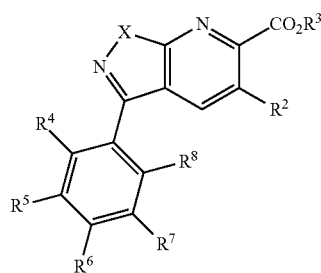

or pharmaceutically acceptable salts or prodrugs thereof. In this class of compounds, X is O or $NR^1$, wherein $R^1$ is hydrogen or substituted or unsubstituted alkyl; $R^2$ is hydrogen or substituted or unsubstituted alkyl; $R^3$ is hydrogen, substituted or unsubstituted alkyl, or substituted or unsubstituted cycloalkyl; and $R^4$, $R^5$, $R^6$, $R^7$, and $R^8$ are each independently selected from the group consisting of hydrogen, halogen, hydroxyl, substituted or unsubstituted alkyl, and substituted or unsubstituted aryl.

Also described herein is a composition comprising one or more of the compounds described herein and a pharmaceutically acceptable carrier.

A method for the treatment of a protein folding disorder in a subject is also described herein. The method for the treatment of a protein folding disorder in a subject comprises administering to the subject an effective amount of a compound as described herein. Optionally, the protein folding disorder is cystic fibrosis.

Also provided herein are methods of rescuing halide efflux in a cell, correcting a processing defect of a delF508-CFTR protein in a cell, and correcting functional delF508-CFTR chloride channels in a cell. The method of rescuing halide efflux in a cell comprises contacting a cell with a compound as described herein, wherein the cell endogenously expresses a CFTR mutation. Optionally, the CFTR mutation is delF508-CFTR. Optionally, the halide efflux is chloride efflux.

A method of correcting a processing defect of a delF508-CFTR protein in a cell comprises contacting a cell with a compound as described herein, wherein the cell expresses a delF508-CFTR mutation. Optionally, the cell is a CF human airway epithelial cell or a CF human lung cell.

A method of correcting functional delF508-CFTR chloride channels in a cell comprises contacting a cell with a compound as described herein, wherein the cell is a polarized epithelial cell. Optionally, the method is performed in vitro. Optionally, the method is performed in vivo.

DETAILED DESCRIPTION

Figure 1:
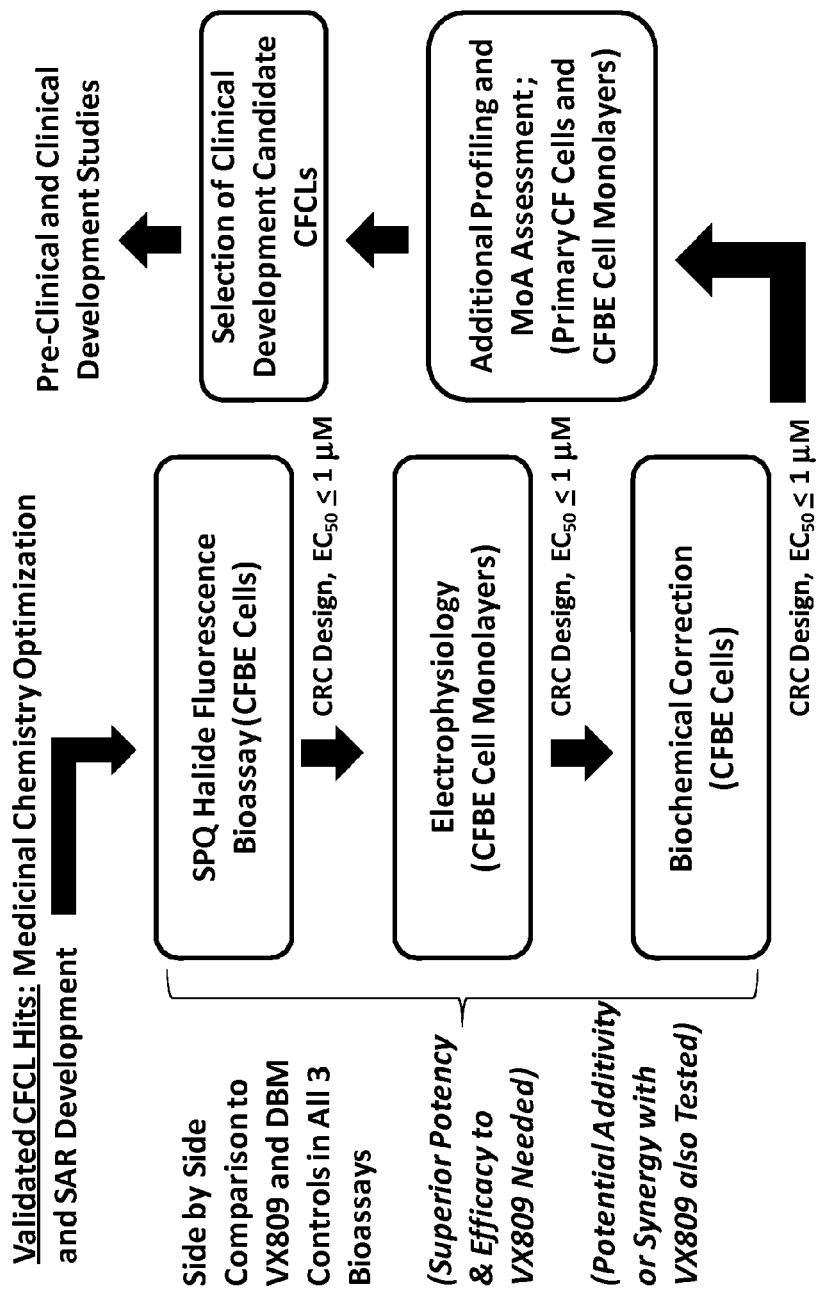
FIG. 1 is a schematic showing a general approach for identifying delF508-CFTR correctors.
Figure 2:
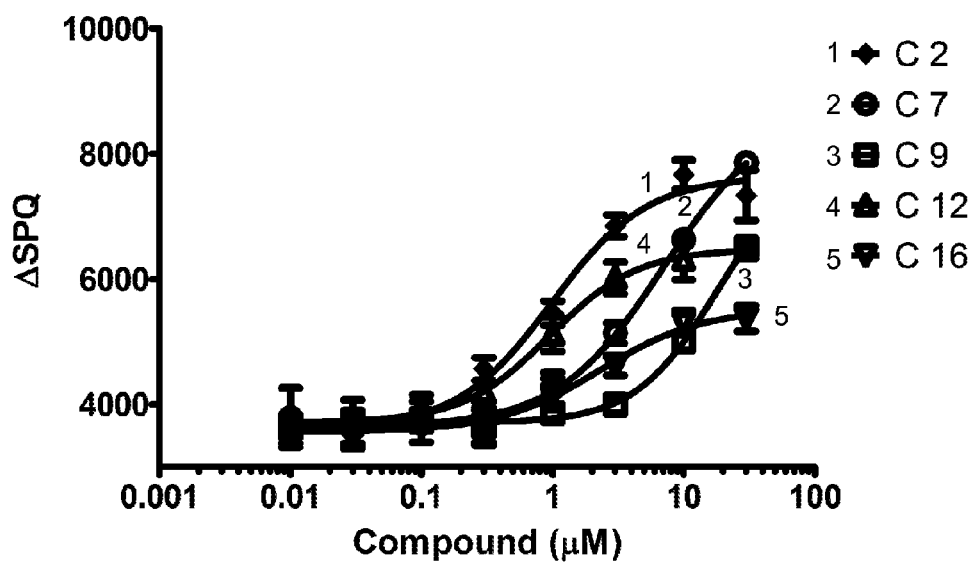
FIG. 2 is a graph demonstrating the ΔSPQ measurements from SPQ high throughput screening assays for Compounds C-2, C-7, C-9, C-12, and C-16 at increasing dosages.
Figure 3:
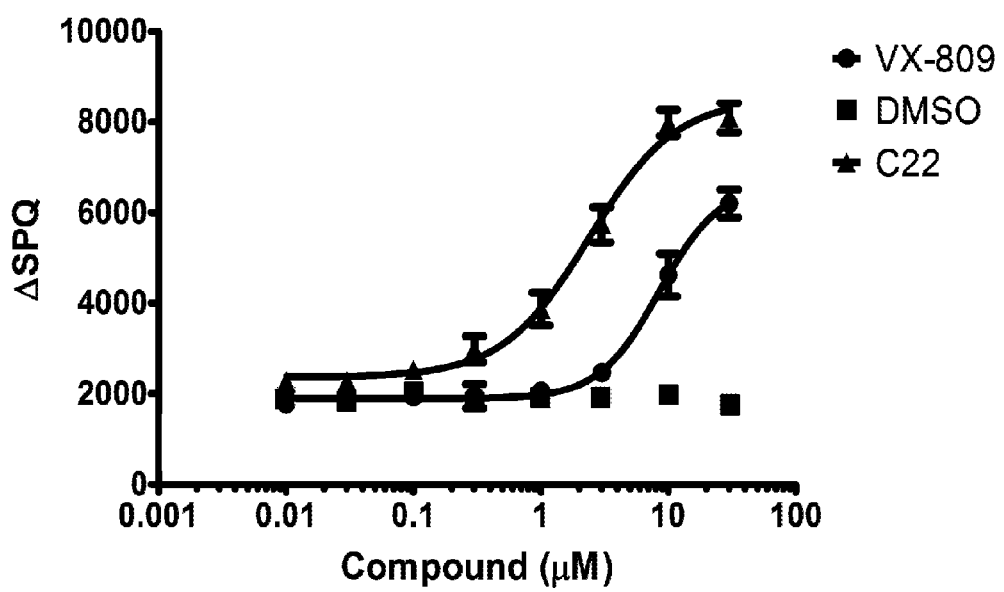
FIG. 3 is a graph demonstrating the ΔSPQ measurements from SPQ high throughput screening assays for VX-809, DMSO, and Compound C-22.
Figure 4:
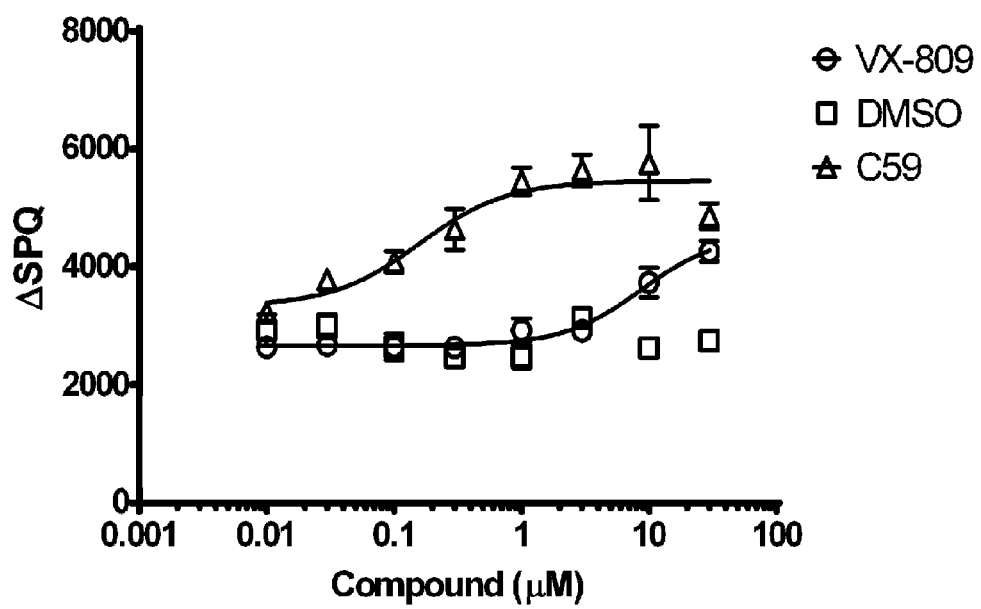
FIG. 4 is a graph demonstrating the ΔSPQ measurements from SPQ high throughput screening assays for VX-809, DMSO, and Compound C-59.
Figure 5:
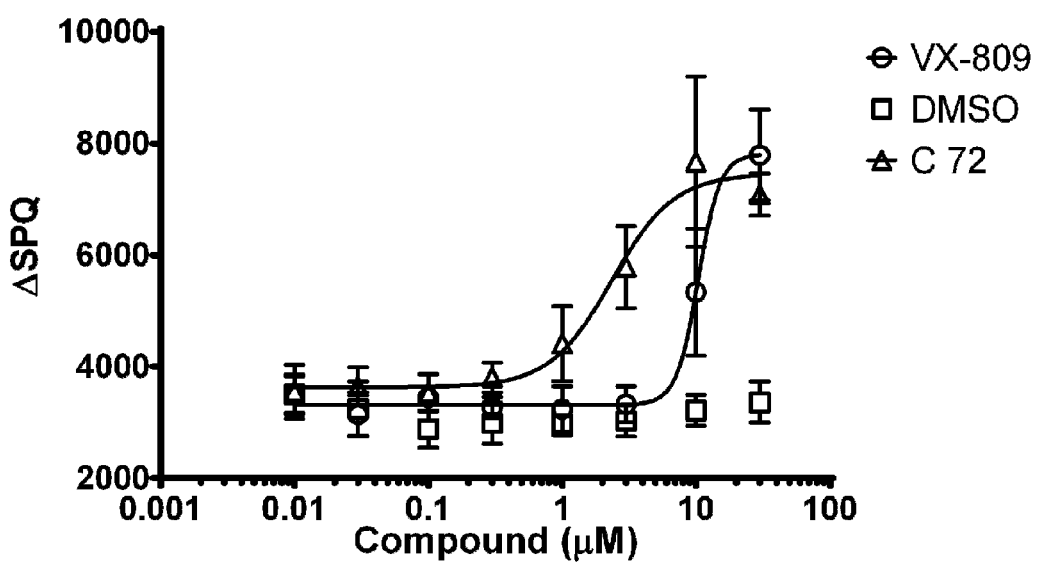
FIG. 5 is a graph demonstrating the ΔSPQ measurements from SPQ high throughput screening assays for VX-809, DMSO, and Compound C-72.

The compounds and methods described herein are useful in the treatment of protein folding disorders. The compounds and methods described herein can be useful, for example, in the treatment of cystic fibrosis, familial hypercholesterolemia, diabetes mellitus, alpha1 antitrypsin deficiency, Fabry's disease, Gaucher's disease, Pompe's disease, hypothyrosis, and Alzheimer's disease. For example, described herein are compounds and methods useful in the treatment of cystic fibrosis. These compounds are able to correct the misfolding or defective trafficking of delF508-CFTR; thus, the compounds are effective as CFTR correctors (i.e., the compounds are effective in rescuing halide efflux in a cell). Methods for screening for CFTR corrector compounds are also described herein.

I. Compounds

A class of CFTR correctors described herein is represented by Formula I:

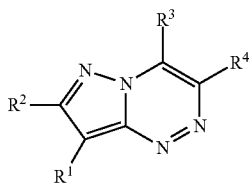

and pharmaceutically acceptable salts or prodrugs thereof.

In Formula I, $R^1$ is substituted or unsubstituted alkyl, substituted or unsubstituted cycloalkyl, or substituted or unsubstituted aryl. Optionally, $R^1$ is substituted phenyl.

Also, in Formula I, $R^2$ is hydrogen, substituted or unsubstituted alkyl, or substituted or unsubstituted aryl. Optionally, $R^2$ is hydrogen or methyl.

Additionally, in Formula I, $R^3$ is hydrogen, substituted or unsubstituted alkyl, substituted or unsubstituted amino, or substituted carbonyl. Optionally, $R^3$ is hydrogen, methyl, or amino.

Further, in Formula I, $R^4$ is substituted or unsubstituted alkyl, substituted carbonyl, substituted or unsubstituted heteroaryl, or substituted or unsubstituted amino. Optionally, $R^4$ is an acidic group. Optionally, $R^4$ is a carbonyl that can be carboxylic acid or an acid derivative. As used herein, an acid derivative refers to a functional derivative of a carboxylic acid such as, for example, an ester, an amide, acylsulphonamide, or tetrazole. Optionally, $R^4$ is —$CO_2H$ or —$CO_2CH_2CH_3$.

As used herein, the terms alkyl and alkenyl include straight- and branched-chain monovalent substituents. Examples include methyl, ethyl, isobutyl, and the like. Ranges of these groups useful with the compounds and methods described herein include $C_1$-$C_8$ alkyl and $C_3$-$C_8$ alkenyl.

Heteroalkyl and heteroalkenyl are defined similarly as alkyl and alkenyl, but can contain O, S, or N heteroatoms or combinations thereof within the backbone. Ranges of these groups useful with the compounds and methods described herein include $C_1$-$C_8$ heteroalkyl and $C_3$-$C_8$ heteroalkenyl.

The terms cycloalkyl and cycloalkenyl include cyclic alkyl groups having a single cyclic ring or multiple condensed rings. Examples include cyclohexyl, cyclopentylethyl, and adamantanyl. Ranges of these groups useful with the compounds and methods described herein include $C_3$-$C_9$ cycloalkyl and $C_5$-$C_9$ cycloalkenyl.

The terms heterocycloalkyl and heterocycloalkenyl are defined similarly as cycloalkyl and cycloalkenyl, but can contain O, S, or N heteroatoms or combinations thereof within the cyclic backbone. Ranges of these groups useful with the compounds and methods described herein include $C_4$-$C_9$ heterocycloalkyl and $C_5$-$C_9$ heterocycloalkenyl.

Aryl groups include, for example, phenyl and substituted phenyl. Heteroaryl groups contain O, N, or S heteroatoms, either alone or in combination in five or six membered rings. Examples of heteroaryl groups with one heteroatom include pyridyl, thienyl, and furyl substituted on or joined by any of the available carbon atoms. Examples of heteroaryl groups with more than one heteroatom include pyrimidinyl, oxazolyl, and thiazolyl substituted on or joined by any of the available carbon atoms. Aryl and heteroaryl groups can include additional fused rings. Examples of such groups include indanyl, naphthyl, benzothienyl, quinolinyl, and isomers thereof substituted on or joined by any of the available carbon atoms.

All groups mentioned above can be unsubstituted or substituted with one or more of the following which may the same or different. Examples of appropriate substituents include, but are not limited to, the following: hydroxyl, halogen, haloalkyl (e.g., trifluoromethyl), amino, alkylamino, dialkylamino, alkylsulphonyl, sulphonamides and reverse sulphonamides, amides and reverse amides, alkyl, heteroalkyl, and cycloalkyl.

In some examples of Formula I, when $R^2$ is methyl, $R^3$ is methyl, and $R^4$ is —$CO_2CH_2CH_3$, then $R^1$ is not p-methoxyphenyl, p-fluorophenyl, or p-chlorophenyl. In some examples of Formula I, when $R^2$ is methyl, $R^3$ is methyl, and $R^4$ is —$CO_2CH_3$, then $R^1$ is not p-chlorophenyl.

In some examples, Formula I is represented by Structure I-A:

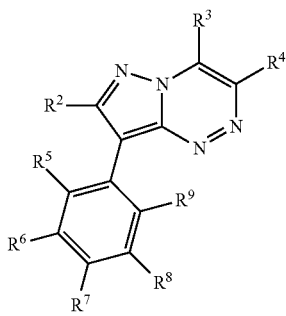

In Structure I-A, $R^2$, $R^3$, and $R^4$ are as defined above for Formula I.

Also, in Structure I-A, $R^5$, $R^6$, $R^7$, $R^8$, and $R^9$ are each independently selected from the group consisting of hydrogen, halogen, hydroxyl, and substituted or unsubstituted alkoxy. Optionally, adjacent R groups in Structure I-A, e.g., $R^5$ and $R^6$, $R^6$ and $R^7$, $R^7$ and $R^8$, or $R^8$ and $R^9$, can be combined to form a substituted or unsubstituted aryl, substituted or unsubstituted cycloalkenyl, substituted or unsubstituted heteroaryl, or substituted or unsubstituted heterocycloalkenyl. For example, $R^6$ and $R^7$ can both be methoxy and can combine to form a dioxane.

In some examples, Formula I is represented by Structure I-B:

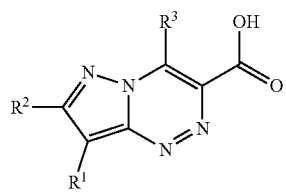

In Structure I-B, $R^1$, $R^2$, and $R^3$ are as defined above for Formula I. Optionally, the compounds according to Structure I-B can be present as the salt (e.g., an ammonium salt).

In some examples, Formula I is represented by Structure I-C:

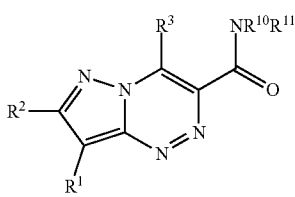

In Structure I-C, $R^1$, $R^2$, and $R^3$ are as defined above for Formula I. Also in Structure I-C, $R^{10}$ and $R^{11}$ are each independently selected from the group consisting of hydrogen and substituted or unsubstituted alkyl.

In some examples, Formula I is represented by Structure I-D:

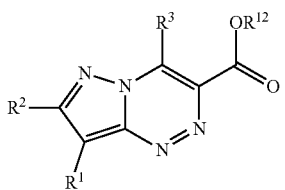

In Structure I-D, $R^1$, $R^2$, and $R^3$ are as defined above for Formula I. Also in Structure I-D, $R^{12}$ is selected from the group consisting of hydrogen, substituted or unsubstituted alkyl, and substituted or unsubstituted cycloalkyl.

Examples of Formula I include the following compounds:

Compound C-1
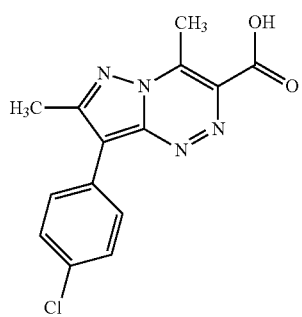

Compound C-2
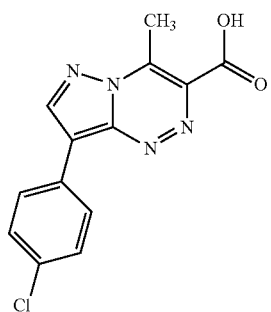

Compound C-3
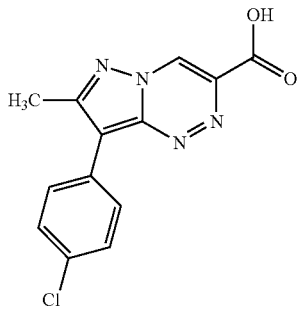

Compound C-4
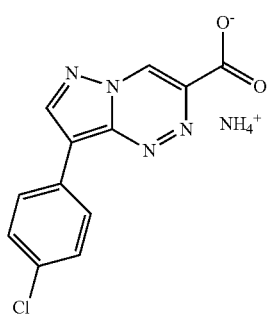

Compound C-5
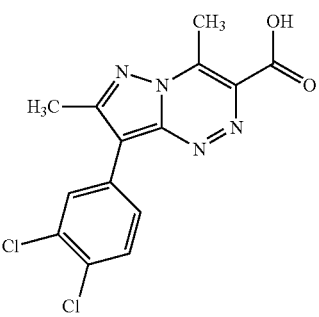

Compound C-6
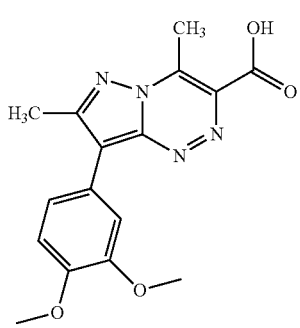

Compound C-7
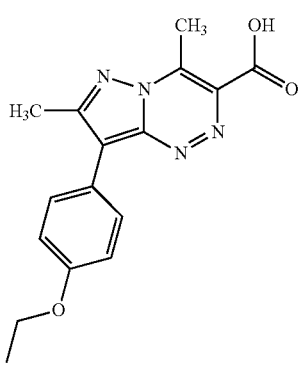

Compound C-8
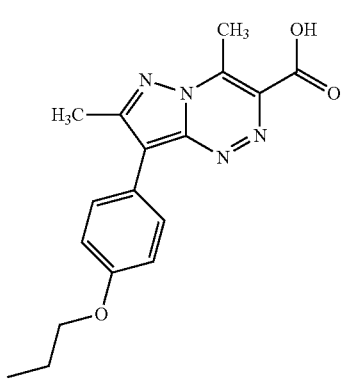
Compound C-9
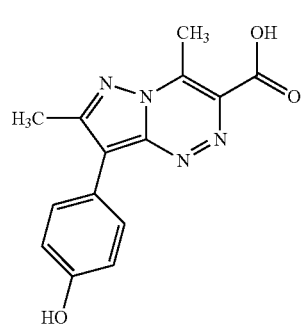
Compound C-10
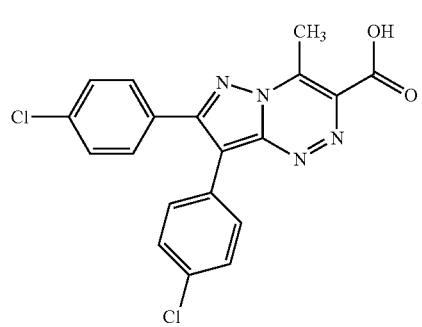
Compound C-11
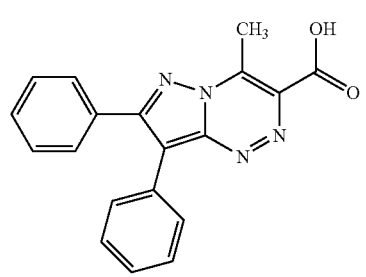
Compound C-12
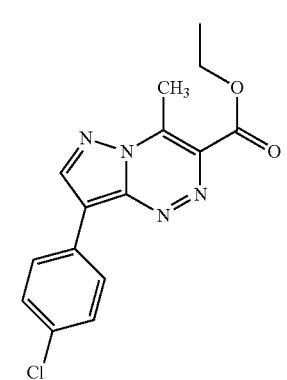
Compound C-13
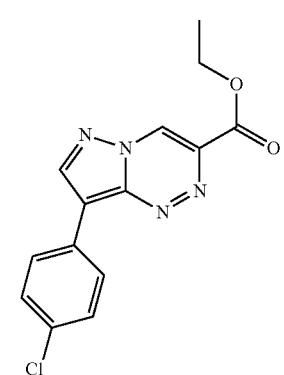
Compound C-14
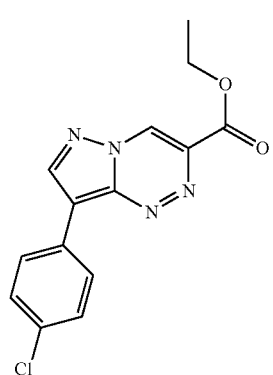
Compound C-15
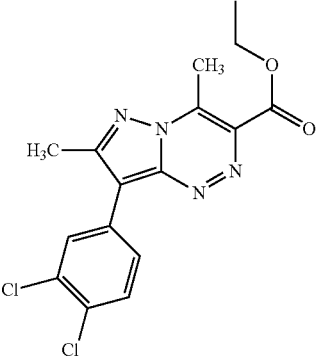
Compound C-16
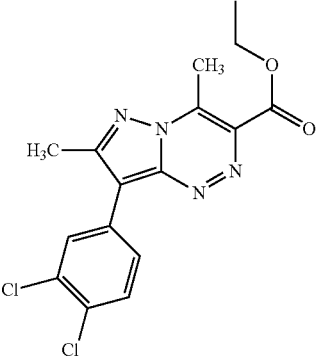

-continued
Compound C-17
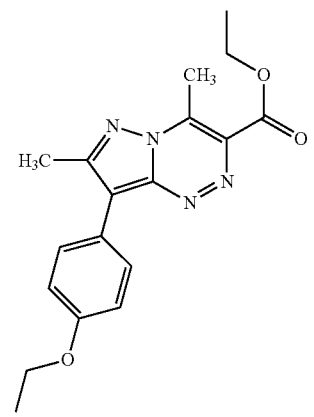
Compound C-18
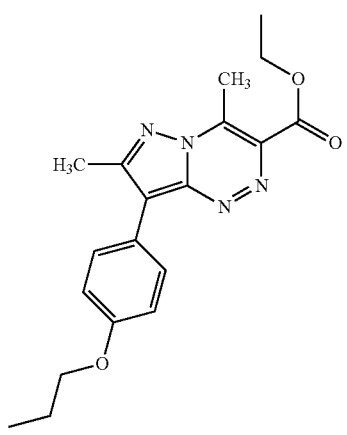
Compound C-19
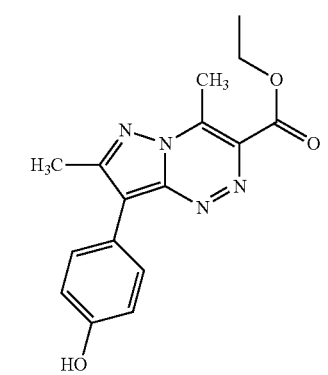
Compound C-20
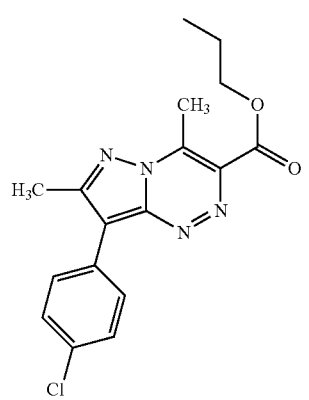
-continued
Compound C-21
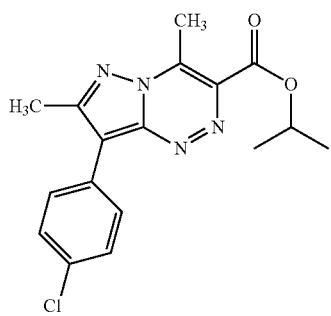
Compound C-22
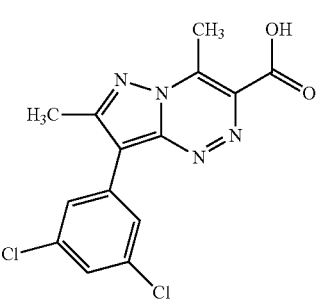
Compound C-23
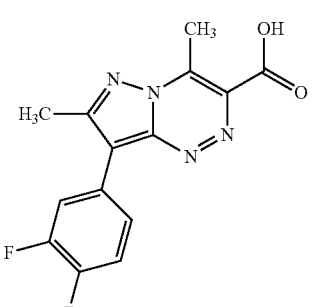
Compond C-24
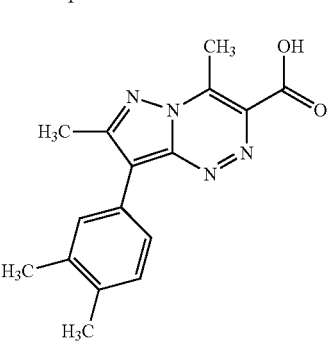
Compound C-25
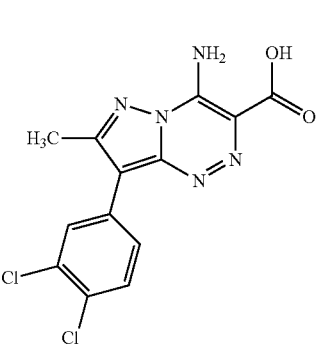

Compound C-26.1
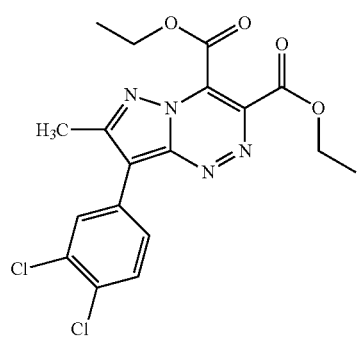
Compound C-26.2
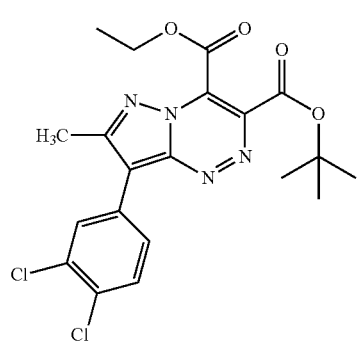
Compound C-27
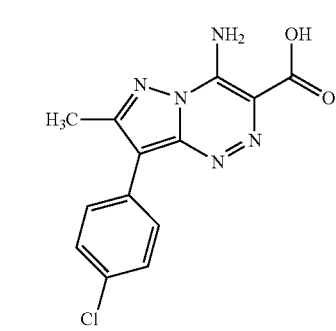
Compound C-28.1
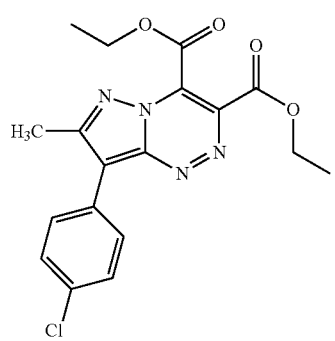
Compound C-29
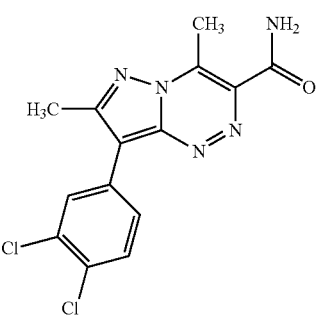
Compound C-30
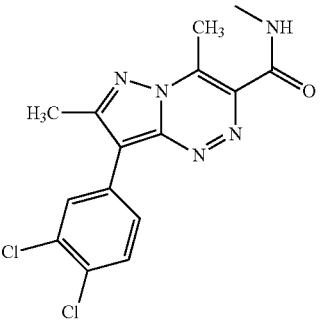
Compound C-31
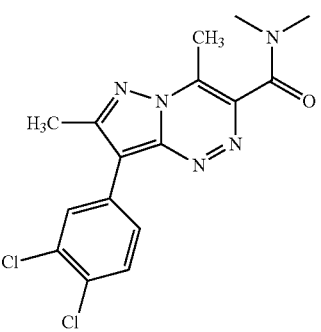
Compound C-32
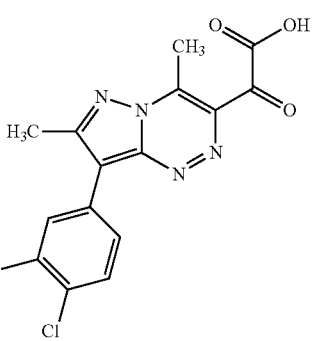

Compound C-32.1
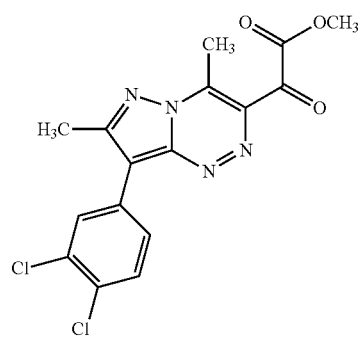
Compound C-37
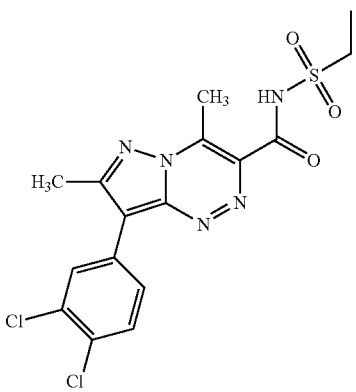
Compound C-34
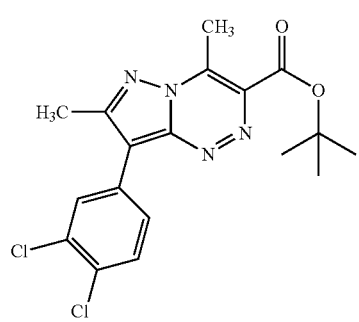
Compound C-40
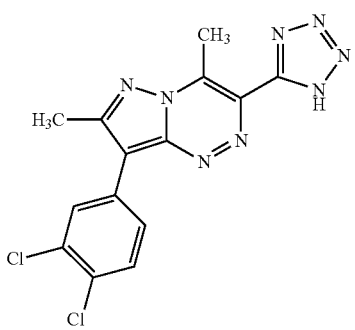
Compound C-35
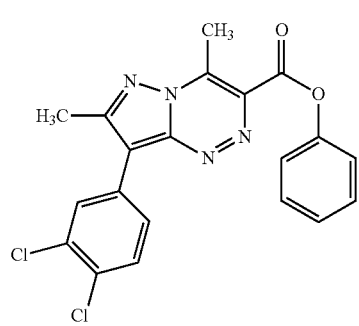
Compound C-41
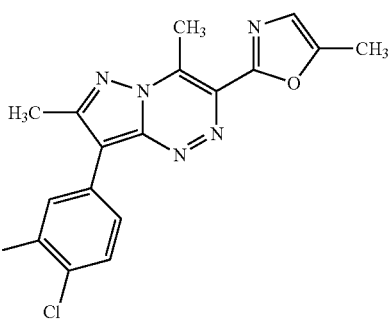
Compound C-36
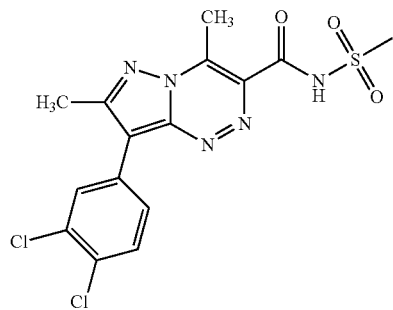
Compound C-42
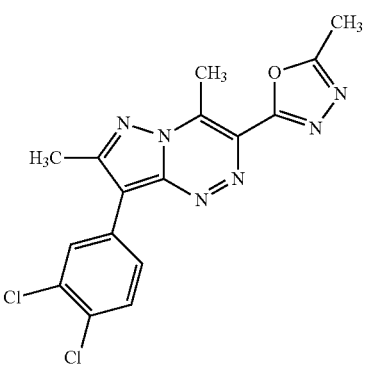

Compound C-43
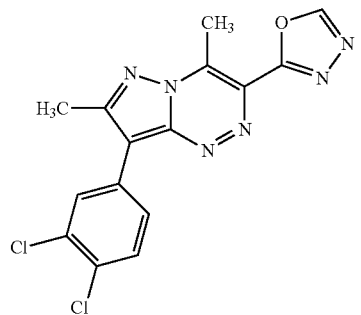
Compound C-49
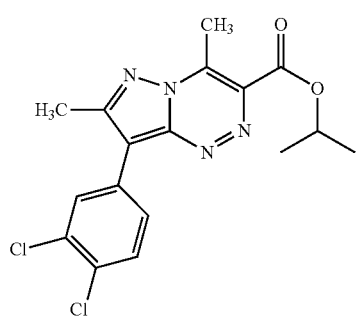
Compound C-50
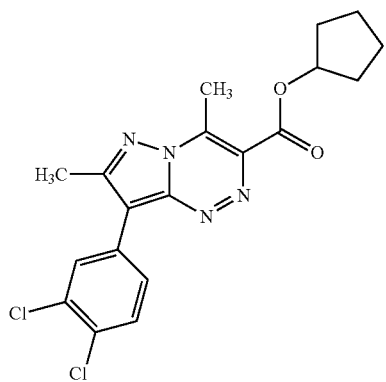
Compound C-51
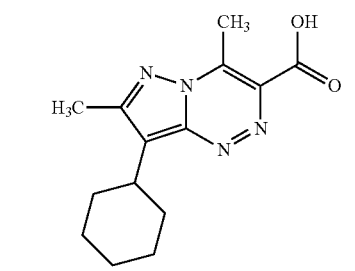
Compound C-52
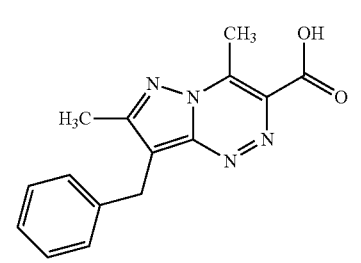
Compound C-53
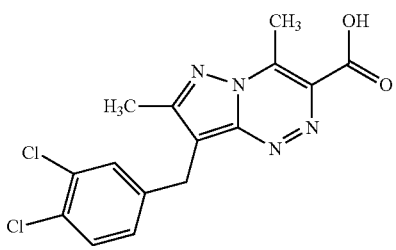
Compound C-54
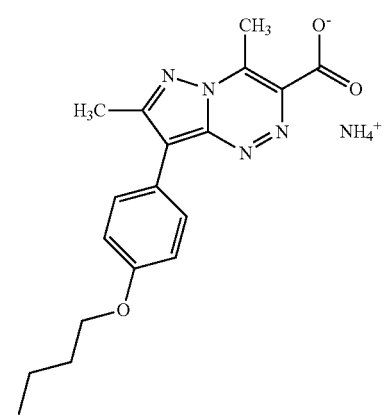
Compound C-55
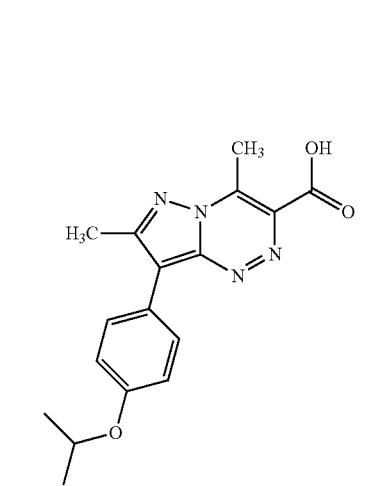
Compound C-56
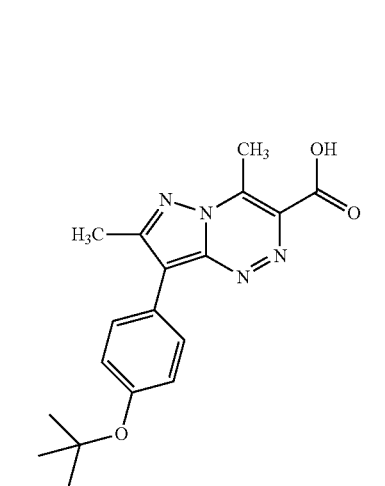

-continued
Compound C-57
Compound C-58
Compound C-59
Compound C-59.1
Compound C-60
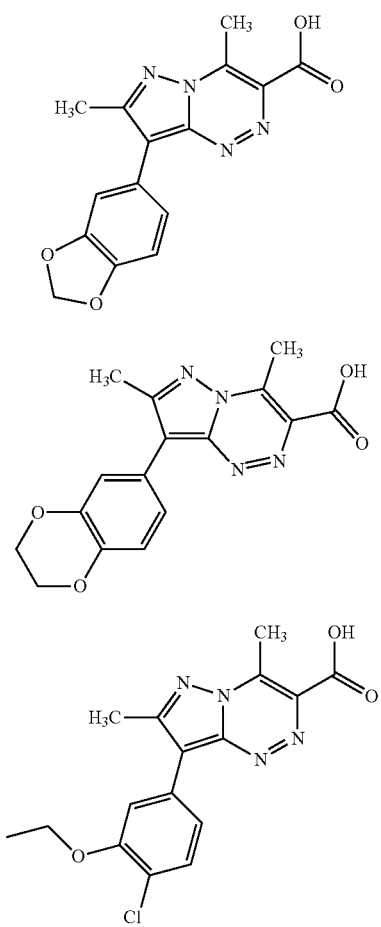
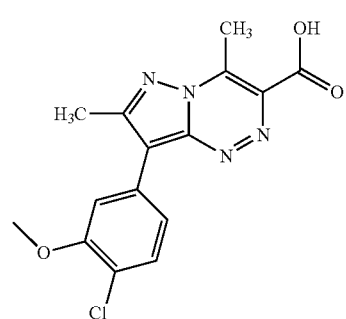
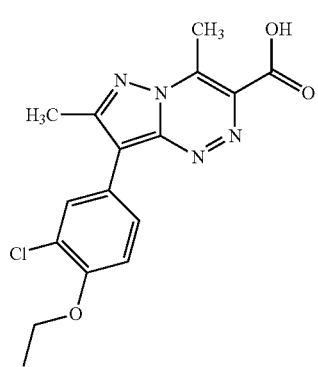
-continued
Compound C-70
Compound C-71
Compound C-71.1
Compound C-72
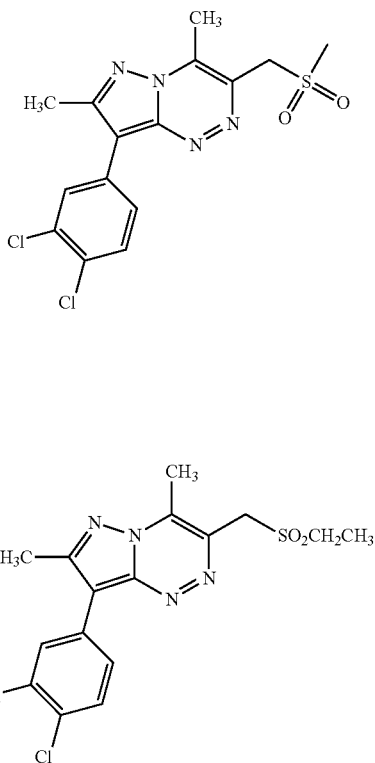
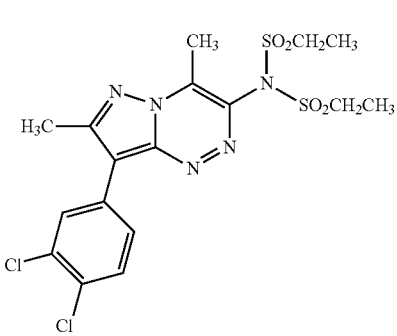

-continued

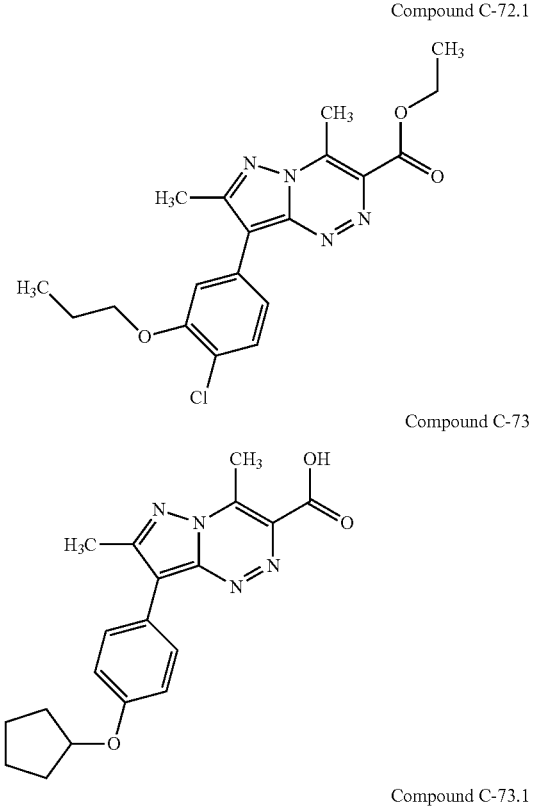

Compound C-72.1

Compound C-73

Compound C-73.1

A class of CFTR correctors described herein is represented by Formula II:

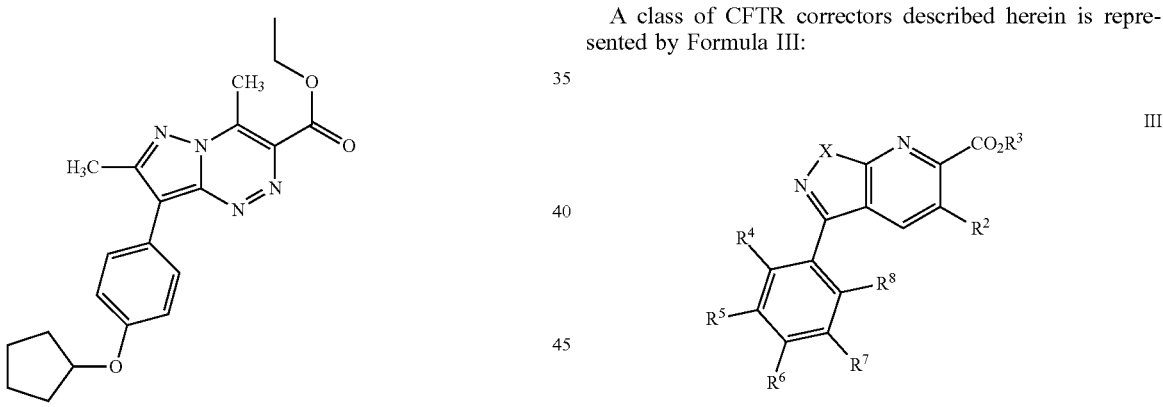

and pharmaceutically acceptable salts or prodrugs thereof.

In Formula II, $R^1$, $R^2$, and $R^3$ are each independently selected from the group consisting of hydrogen and substituted or unsubstituted alkyl. Optionally, $R^1$ is methyl. Optionally, $R^2$ is hydrogen. Optionally, $R^3$ is methyl.

Also, in Formula II, $R^4$, $R^5$, $R^6$, $R^7$, and $R^8$ are each independently selected from the group consisting of hydrogen, halogen, hydroxyl, substituted or unsubstituted alkyl, and substituted or unsubstituted aryl.

An example of Formula II includes the following compound:

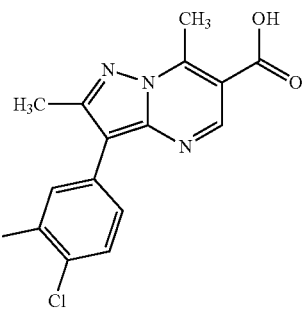

Compound C-45

A class of CFTR correctors described herein is represented by Formula III:

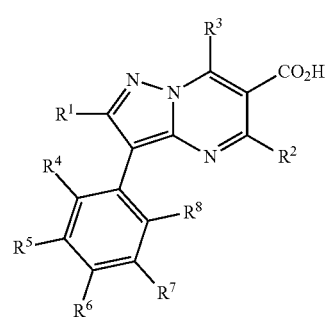

III and pharmaceutically acceptable salts or prodrugs thereof.

In Formula III, X is O or $NR^1$, wherein $R^1$ is hydrogen or substituted or unsubstituted alkyl.

Also, in Formula III, $R^2$ is hydrogen or substituted or unsubstituted alkyl. Optionally, $R^2$ is hydrogen.

Additionally, in Formula III, $R^3$ is hydrogen, substituted or unsubstituted alkyl, or substituted or unsubstituted cycloalkyl.

Further, in Formula III, $R^4$, $R^5$, $R^6$, $R^7$, and $R^8$ are each independently selected from the group consisting of hydrogen, halogen, hydroxyl, substituted or unsubstituted alkyl, or substituted or unsubstituted aryl. Optionally, $R^5$ and $R^6$ are chloro. Optionally, $R^4$, $R^7$, and $R^8$ are hydrogen.

Examples of Formula III include the following compounds:

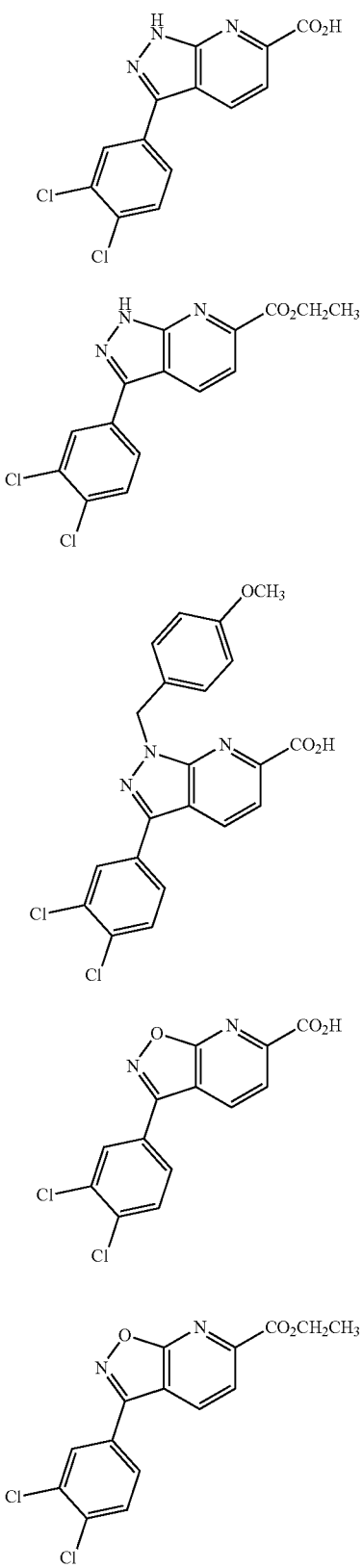

Compound C-66

Compound C-66.1

Compound C-66.2

Compound C-68

Compound C-68.1

An additional compound useful with the methods described herein includes the following compound:

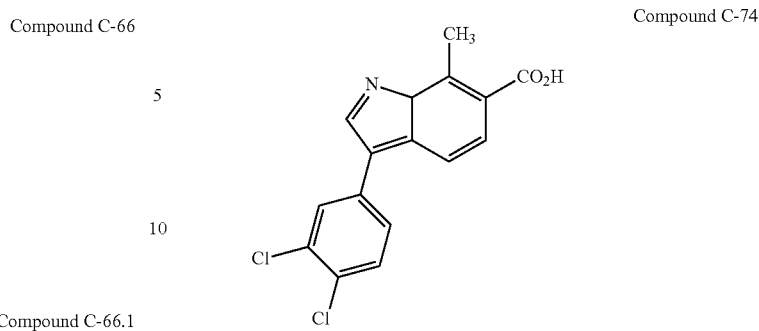

Compound C-74

II. Methods of Making the Compounds

The compounds described herein can be prepared in a variety of ways. The compounds can be synthesized using various synthetic methods. At least some of these methods are known in the art of synthetic organic chemistry. The compounds described herein can be prepared from readily available starting materials. Optimum reaction conditions can vary with the particular reactants or solvent used, but such conditions can be determined by one skilled in the art by routine optimization procedures.

Variations on Formulas I-III and additional compounds described herein include the addition, subtraction, or movement of the various constituents as described for each compound. Similarly, when one or more chiral centers are present in a molecule, all possible chiral variants are included. Additionally, compound synthesis can involve the protection and deprotection of various chemical groups. The use of protection and deprotection, and the selection of appropriate protecting groups can be determined by one skilled in the art. The chemistry of protecting groups can be found, for example, in Greene, et al., Protective Groups in Organic Synthesis, 2d. Ed., Wiley & Sons, 1991, which is incorporated herein by reference in its entirety.

Reactions to produce the compounds described herein can be carried out in solvents, which can be selected by one of skill in the art of organic synthesis. Solvents can be substantially nonreactive with the starting materials (reactants), the intermediates, or products under the conditions at which the reactions are carried out, i.e., temperature and pressure. Reactions can be carried out in one solvent or a mixture of more than one solvent. Product or intermediate formation can be monitored according to any suitable method known in the art. For example, product formation can be monitored by spectroscopic means, such as nuclear magnetic resonance spectroscopy (e.g., $^1H$ or $^{13}C$) infrared spectroscopy, spectrophotometry (e.g., UV-visible), or mass spectrometry, or by chromatography such as high performance liquid chromatography (HPLC) or thin layer chromatography.

III. Pharmaceutical Formulations

One or more of the compounds described herein or pharmaceutically acceptable salts or prodrugs thereof can be provided in a pharmaceutical composition comprising a pharmaceutical carrier. Furthermore, the one or more compounds described herein can be combined with other agents, including treatments for lung, digestive, hepatic, and biliary tract related diseases and disorders. For example, in the case of cystic fibrosis, the compounds described herein can be combined with mucus thinning drugs (e.g., dornase alfa, N-Acetyl cysteine, and hypertonic saline), bronchodilators (e.g., metaproterenol sulfate, pirbuterol acetate, salmeterol, albuterol, and terbutaline sulfate), P2Y2-receptor agonists (e.g., denufosol), and agents that target nonsense mutations (e.g., PTC124). Further examples of additional agents that can be combined with the compounds described herein include antibiotics (e.g., aminoglycosides, antipseudomonal penicillins, and cephalosporins), antimicrobial drugs (e.g., rifabutin), ethambutol, clarithromycin, clofazimine, aztreonam, steroidal and nonsteroidal anti-inflammatory drugs (e.g., ibuprofen and prednisone), pentoxifylline, dornase alfa, and ursodeoxycholic acid.

The one or more compounds described herein can be provided as pharmaceutical compositions administered in combination with one or more other therapeutic or prophylactic agents. As used throughout, a therapeutic agent is a compound or composition effective in ameliorating a pathological condition. Illustrative examples of therapeutic agents include, but are not limited to, chemotherapeutic agents, anti-viral agents, anti-opportunistic agents, antibiotics, and immunostimulatory agents. Optionally, more than one therapeutic agent is administered in combination with the provided compositions.

The one or more compounds described herein, with or without additional agents, can be provided in the form of an inhaler or nebulizer for inhalation therapy. As used herein, inhalation therapy refers to the delivery of a therapeutic agent, such as the compounds described herein, in an aerosol form to the respiratory tract (i.e., pulmonary delivery). As used herein, the term aerosol refers to very fine liquid or solid particles carried by a propellant gas under pressure to a site of therapeutic application. When a pharmaceutical aerosol is employed, the aerosol contains the one or more compounds described herein, which can be dissolved, suspended, or emulsified in a mixture of a fluid carrier and a propellant. The aerosol can be in the form of a solution, suspension, emulsion, powder, or semi-solid preparation. Aerosols employed are intended for administration as fine, solid particles or as liquid mists via the respiratory tract of a patient.

The propellant of an aerosol package containing the one or more compounds described herein can be capable of developing pressure within the container to expel the compound when a valve on the aerosol package is opened. Various types of propellants can be utilized, such as fluorinated hydrocarbons (e.g., trichloromonofluromethane, dichlorodifluoromethane, and dichlorotetrafluoroethane) and compressed gases (e.g., nitrogen, carbon dioxide, nitrous oxide, or Freon). The vapor pressure of the aerosol package can be determined by the propellant or propellants that are employed. By varying the proportion of each component propellant, any desired vapor pressure can be obtained within the limits of the vapor pressure of the individual propellants.

As described above, the one or more compounds described herein can be provided with a nebulizer, which is an instrument that generates very fine liquid particles of substantially uniform size in a gas. The liquid containing the one or more compounds described herein can be dispersed as droplets about 5 mm or less in diameter in the form of a mist. The small droplets can be carried by a current of air or oxygen through an outlet tube of the nebulizer. The resulting mist can penetrate into the respiratory tract of the patient.

Additional inhalants useful for delivery of the compounds described herein include intra-oral sprays, mists, metered dose inhalers, and dry powder generators (See Gonda, *J. Pharm. Sci.* 89:940-945, 2000, which is incorporated herein by reference in its entirety, at least, for inhalation delivery methods taught therein). For example, a powder composition containing the one or more compounds as described herein, with or without a lubricant, carrier, or propellant, can be administered to a patient. The delivery of the one or more compounds in powder form can be carried out with a conventional device for administering a powder pharmaceutical composition by inhalation.

Depending on the intended mode of administration, the pharmaceutical composition can be in the form of solid, semi-solid, or liquid dosage forms, such as, for example, tablets, suppositories, pills, capsules, powders, liquids, aerosols, or suspensions, preferably in unit dosage form suitable for single administration of a precise dosage. The compositions will include a therapeutically effective amount of the compound described herein or derivatives thereof in combination with a pharmaceutically acceptable carrier and, in addition, can include other medicinal agents, pharmaceutical agents, carriers, or diluents. By pharmaceutically acceptable is meant a material that is not biologically or otherwise undesirable, which can be administered to an individual along with the selected compound without causing unacceptable biological effects or interacting in a deleterious manner with the other components of the pharmaceutical composition in which it is contained.

As used herein, the term carrier encompasses any excipient, diluent, filler, salt, buffer, stabilizer, solubilizer, lipid, stabilizer, or other material well known in the art for use in pharmaceutical formulations. The choice of a carrier for use in a composition will depend upon the intended route of administration for the composition. The preparation of pharmaceutically acceptable carriers and formulations containing these materials is described in, e.g., Remington's Pharmaceutical Sciences, 21st Edition, ed. University of the Sciences in Philadelphia, Lippincott, Williams & Wilkins, Philadelphia Pa., 2005. Examples of physiologically acceptable carriers include buffers such as phosphate buffers, citrate buffer, and buffers with other organic acids; antioxidants including ascorbic acid; low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN® (ICI, Inc.; Bridgewater, N.J.), polyethylene glycol (PEG), and PLURONICS™ (BASF; Florham Park, N.J.).

Compositions containing the compounds as described herein or pharmaceutically acceptable salts or prodrugs thereof suitable for parenteral injection can comprise physiologically acceptable sterile aqueous or nonaqueous solutions, dispersions, suspensions or emulsions, and sterile powders for reconstitution into sterile injectable solutions or dispersions. Examples of suitable aqueous and nonaqueous carriers, diluents, solvents, or vehicles include water, ethanol, polyols (propyleneglycol, polyethyleneglycol, glycerol, and the like), suitable mixtures thereof, vegetable oils (such as olive oil), and injectable organic esters such as ethyl oleate. Proper fluidity can be maintained, for example, by the use of a coating such as lecithin, by the maintenance of the required particle size in the case of dispersions, and by the use of surfactants.

These compositions can also contain adjuvants such as preserving, wetting, emulsifying, and dispensing agents. Prevention of the action of microorganisms can be promoted by various antibacterial and antifungal agents, for example, parabens, chlorobutanol, phenol, sorbic acid, and the like. Isotonic agents, for example, sugars, sodium chloride, and the like can also be included. Prolonged absorption of the injectable pharmaceutical form can be brought about by the use of agents delaying absorption, for example, aluminum monostearate and gelatin.

Solid dosage forms for oral administration of the compounds described herein or pharmaceutically acceptable salts or prodrugs thereof include capsules, tablets, pills, powders, and granules. In such solid dosage forms, one or more of the compounds described herein or derivatives thereof is admixed with at least one inert customary excipient (or carrier) such as sodium citrate or dicalcium phosphate or (a) fillers or extenders, as for example, starches, lactose, sucrose, glucose, mannitol, and silicic acid, (b) binders, as for example, carboxymethylcellulose, alignates, gelatin, polyvinylpyrrolidone, sucrose, and acacia, (c) humectants, as for example, glycerol, (d) disintegrating agents, as for example, agar-agar, calcium carbonate, potato or tapioca starch, alginic acid, certain complex silicates, and sodium carbonate, (e) solution retarders, as for example, paraffin, (f) absorption accelerators, as for example, quaternary ammonium compounds, (g) wetting agents, as for example, cetyl alcohol, and glycerol monostearate, (h) adsorbents, as for example, kaolin and bentonite, and (i) lubricants, as for example, talc, calcium stearate, magnesium stearate, solid polyethylene glycols, sodium lauryl sulfate, or mixtures thereof. In the case of capsules, tablets, and pills, the dosage forms can also comprise buffering agents.

Solid compositions of a similar type can also be employed as fillers in soft and hard-filled gelatin capsules using such excipients as lactose or milk sugar as well as high molecular weight polyethyleneglycols, and the like.

Solid dosage forms such as tablets, dragees, capsules, pills, and granules can be prepared with coatings and shells, such as enteric coatings and others known in the art. They can contain opacifying agents and can also be of such composition that they release the active compound or compounds in a certain part of the intestinal tract in a delayed manner. Examples of embedding compositions that can be used are polymeric substances and waxes. The active compounds can also be in micro-encapsulated form, if appropriate, with one or more of the above-mentioned excipients.

Liquid dosage forms for oral administration of the compounds described herein or pharmaceutically acceptable salts or prodrugs thereof include pharmaceutically acceptable emulsions, solutions, suspensions, syrups, and elixirs. In addition to the active compounds, the liquid dosage forms can contain inert diluents commonly used in the art, such as water or other solvents, solubilizing agents, and emulsifiers, as for example, ethyl alcohol, isopropyl alcohol, ethyl carbonate, ethyl acetate, benzyl alcohol, benzyl benzoate, propyleneglycol, 1,3-butyleneglycol, dimethylformamide, oils, in particular, cottonseed oil, groundnut oil, corn germ oil, olive oil, castor oil, sesame oil, glycerol, tetrahydrofurfuryl alcohol, polyethyleneglycols, and fatty acid esters of sorbitan, or mixtures of these substances, and the like.

Besides such inert diluents, the composition can also include additional agents, such as wetting, emulsifying, suspending, sweetening, flavoring, or perfuming agents.

Suspensions, in addition to the active compounds, can contain additional agents, as for example, ethoxylated isostearyl alcohols, polyoxyethylene sorbitol and sorbitan esters, microcrystalline cellulose, aluminum metahydroxide, bentonite, agar-agar and tragacanth, or mixtures of these substances, and the like.

Compositions of the compounds described herein or pharmaceutically acceptable salts or prodrugs thereof for rectal administration are optionally suppositories, which can be prepared by mixing the compounds with suitable non-irritating excipients or carriers such as cocoa butter, polyethyleneglycol or a suppository wax, which are solid at ordinary temperatures but liquid at body temperature and therefore, melt in the rectum or vaginal cavity and release the active component.

Dosage forms for topical administration of the compounds described herein or pharmaceutically acceptable salts or prodrugs thereof include ointments, powders, sprays, aerosols, and inhalants (e.g., intra-oral sprays, mists, metered dose inhalers, nebulizers, and dry powder generators). The compounds described herein or pharmaceutically salts or prodrugs thereof are admixed under sterile conditions with a physiologically acceptable carrier and any preservatives, buffers, or propellants as can be required. Ophthalmic formulations, ointments, powders, and solutions are also contemplated as being within the scope of the compositions.

The term pharmaceutically acceptable salts as used herein refers to those salts of the compound described herein or derivatives thereof that are, within the scope of sound medical judgment, suitable for use in contact with the tissues of subjects without undue toxicity, irritation, allergic response, and the like, commensurate with a reasonable benefit/risk ratio, and effective for their intended use, as well as the zwitterionic forms, where possible, of the compounds described herein. The term salts refers to the relatively non-toxic, inorganic and organic acid addition salts of the compounds described herein. These salts can be prepared in situ during the isolation and purification of the compounds or by separately reacting the purified compound in its free base form with a suitable organic or inorganic acid and isolating the salt thus formed. Representative salts include the hydrobromide, hydrochloride, sulfate, bisulfate, nitrate, acetate, oxalate, valerate, oleate, palmitate, stearate, laurate, borate, benzoate, lactate, phosphate, tosylate, citrate, maleate, fumarate, succinate, tartrate, naphthylate mesylate, glucoheptonate, lactobionate, methane sulphonate, and laurylsulphonate salts, and the like. These can include cations based on the alkali and alkaline earth metals, such as sodium, lithium, potassium, calcium, magnesium, and the like, as well as non-toxic ammonium, quaternary ammonium, and amine cations including, but not limited to ammonium, tetramethylammonium, tetraethylammonium, methylamine, dimethylamine, trimethylamine, triethylamine, ethylamine, and the like. (See Stahl and Wermuth, Pharmaceutical Salts: Properties, Selection, and Use, Wiley-VCH, 2008, which is incorporated herein by reference in its entirety, at least, for compositions taught therein.)

Administration of compounds described herein or pharmaceutically acceptable salts or prodrugs thereof can be carried out using therapeutically effective amounts of the compounds described herein or pharmaceutically acceptable salts or prodrugs thereof for periods of time effective to treat neurological disorders. The effective amount of the compounds described herein or pharmaceutically acceptable salts or prodrugs thereof can be determined by one of ordinary skill in the art and includes exemplary dosage amounts for a mammal of from about 0.5 to about 200 mg/kg of body weight of active compound per day, which can be administered in a single dose or in the form of individual divided doses, such as from 1 to 4 times per day. Alternatively, the dosage amount can be from about 0.5 to about 150 mg/kg of body weight of active compound per day, about 0.5 to 100 mg/kg of body weight of active compound per day, about 0.5 to about 75 mg/kg of body weight of active compound per day, about 0.5 to about 50 mg/kg of body weight of active compound per day, about 0.5 to about 25 mg/kg of body weight of active compound per day, about 1 to about 20 mg/kg of body weight of active compound per day, about 1 to about 10 mg/kg of body weight of active compound per day, about 20 mg/kg of body weight of active compound per day, about 10 mg/kg of body weight of active compound per day, or about 5 mg/kg of body weight of active compound per day. Those of skill in the art will understand that the specific dose level and frequency of dosage for any particular subject can be varied and will depend upon a variety of factors, including the activity of the specific compound employed, the metabolic stability and length of action of that compound, the species, age, body weight, general health, sex and diet of the subject, the mode and time of administration, rate of excretion, drug combination, and severity of the particular condition.

IV. Methods of Use

The methods described herein include a method of treating protein folding disorders (e.g., cystic fibrosis) in a subject. These methods include the step of administering to the subject a compound of the structures described herein. Additional steps can be included in the method described herein. For example, the methods can further include the steps of selecting a subject with a protein folding disorder, such as cystic fibrosis, and administering to the subject one or more of the CFTR correctors described herein.

In the methods described herein, the subjects treated can be further treated with one or more additional agents. The one or more additional agents and the compounds described herein or pharmaceutically acceptable salts or prodrugs thereof can be administered together in a single composition (e.g., as an admixture) or in separate compositions in any order, including simultaneous administration, as well as temporally spaced order of up to several days apart. The methods can also include more than a single administration of the one or more additional agents and/or the compounds described herein or pharmaceutically acceptable salts or prodrugs thereof. The administration of the one or more additional agents and the compounds described herein or pharmaceutically acceptable salts or prodrugs thereof can be by the same or different routes and concurrently or sequentially.

As described above, the compounds described herein are useful in the treatment of protein folding disorders. Examples of protein folding disorders include cystic fibrosis; neurodegenerative diseases such as Alzheimer's disease, Parkinson's disease, Creutzfeld-Jakob disease, Kuru, GSS disease, Huntington's disease, Polyglutamine diseases, Prion disease, Bovine Spongiform Encephalopathy (BSE), Amyotrophic Lateral Sclerosis, Alexander's disease, Primary Systemic Amyloidosis, Secondary Systemic Amyloidosis, Senile Systemic Amyloidosis, and Amyloidosis in senescence; ocular diseases such as Cataract, Retinitis Pigmentosa, and Macular Degeneration; and other diseases such as Islet amyloid, Medullar Carcinoma of the Thyroid, Hereditary Renal Amyloidosis, Hemodialysis-related amyloidosis, Desmin-related Cardiomyopathy, Charcot-Marie Tooth disease, diabetes insipidis, alpha1 antitrypsin deficiency, Fabry's disease, Gaucher's disease, and Pompe's disease. The compounds described herein are also useful in the treatment of chronic obstructive pulmonary diseases (COPD), including chronic bronchitis and/or emphysema (e.g., emphysema caused by smoking or by exposure to smoke). CFTR mRNA and protein are down-regulated in the COPD umbrella of diseases.

The compounds described herein are also useful in rescuing halide efflux in a cell, correcting the protein processing defect in a cell, and correcting functional delF508-CFTR chloride channels in a cell. The methods of rescuing halide efflux in a cell include contacting a cell with a compound as described herein. In these methods, the cell endogenously expresses a CFTR mutation. Optionally, the CFTR mutation is delF508-CFTR. Optionally, the halide efflux is chloride efflux.

The methods of correcting a processing defect of a delF508-CFTR protein in a cell include contacting a cell with a compound as described herein. In these methods, the cell expresses a delF508-CFTR mutation. Optionally, the cell is a CF human airway epithelial cell or a CF human lung.

The methods of correcting functional delF508-CFTR chloride channels in a cell include contacting a cell with a compound as described herein. Optionally, the chloride channels are in the apical membrane of a polarized epithelial cell. Optionally, the method is performed in vitro or in vivo.

V. Methods of Profiling

Additionally, a method of profiling a compound for treating cystic fibrosis (i.e., a CFTR corrector) is provided. The methods employ assays that can gauge the relative potency and efficacy of the compounds described herein, as compared to a control, for treating a protein folding disorder such as cystic fibrosis. The methods optionally include a CF bronchial epithelial cell that endogenously expresses a CFTR mutation (e.g., the delF508-CFTR mutation). The cell can be, for example, a primary or immortal CF lung and/or airway epithelial cell (e.g., CFBE41o– cells). CFBE41o– cells are human airway epithelial cells on a delF508-CFTR homozygous background. Optionally, the cells do not over-express the CFTR mutation.

The cell models used in other methods of identifying CFTR correctors have employed low temperature, chemical chaperones such as glycerol, 4-phenylbutyrate, DMSO, and overexpression of CFTR in a transduced Fisher rat thyroid cell line as the model. The present methods do not require, and optionally exclude, over-expression of CFTR, low temperature, and chemical chaperones, which are variables that can distort the results.

The method of profiling can include detecting the rescue of halide efflux from a cell. The step of detecting a rescue of halide efflux from the cell can be monitored using the halide quenched dye 6-methoxy-N-(3-sulfopropyl)-quinolinium (SPQ, Molecular Probes Inc., Eugene, Oreg.). In this method, cells are treated with a compound as described herein for a period of time (e.g., 48 hours). The rescue or correction of halide efflux is then detected using the SPQ assay with the halide dye. The degree of halide efflux rescue or correction indicates that the compound has corrected delF508-CFTR-driven membrane chloride ion transport and is, therefore, useful in treating cystic fibrosis. Optionally, the halide efflux is chloride efflux. The method of screening can further comprise performing the method with multiple concentrations of the compound.

The method of profiling can also include determining the degree of CFTR glycosylation or CFTR protein processing. Optionally, this method can be performed using Western blot analysis. In this method, cells can be treated with the compound as described herein for a period of time (e.g., 24 hours) and, optionally, at multiple concentrations (e.g., 4 doses).

The method of profiling can further include determining the degree of functional delF508-CFTR chloride ion channels in the apical cell membrane of cells (e.g., polarized CF human airway epithelial cells). This method can use electrophysiological methods, such as Ussing chamber-based measurement of short-circuit current, voltammeter-based measurement of open-circuit transepithelial voltage and transepithelial resistance, and patch-clamp electrophysiology.

In general, compounds useful for treating cystic fibrosis can be identified from large libraries of natural products or synthetic (or semi-synthetic) extracts or chemical libraries according to methods known in the art. The precise source of test extracts or compounds is not critical to the screening procedure(s). Accordingly, virtually any number of chemical extracts or compounds can be screened using the methods described herein. Examples of such extracts or compounds include, but are not limited to, plant-, fungal-, prokaryotic- or animal-based extracts, fermentation broths, and synthetic compounds, as well as modifications of existing compounds. Numerous methods are also available for generating random or directed synthesis (e.g., semi-synthesis or total synthesis) of any number of chemical compounds, including, but not limited to, saccharide-, lipid-, peptide-, polypeptide- and nucleic acid-based compounds. Synthetic compound libraries and libraries of natural compounds in the form of bacterial, fungal, plant, and animal extracts are commercially available. In addition, natural and synthetically produced libraries are generated, if desired, according to methods known in the art, e.g., by standard extraction and fractionation methods. Furthermore, if desired, any library or compound is readily modified using standard chemical, physical, or biochemical methods.

As used herein, the terms treatment, treating, or treat refer to a method of reducing or delaying the onset of one or more signs or symptoms or an improvement in the clinical state of the subject being treated for a disease or disorder (e.g., cystic fibrosis). Thus, in the disclosed method, treatment can refer to a 10%, 20%, 30%, 40%, 50%, 60%, 70%, 80%, 90%, or 100% reduction in the severity of one or more symptoms of a disease or condition. For example, reduced numbers of infections or hospitalizations, reduction in respiratory or gastrointestinal symptoms, improved nutritional status, or improved pulmonary function in the subject as compared to a control indicate effective treatment. As used herein, control refers to the untreated condition (e.g., the subject not treated with the compounds and compositions described herein). Thus, the reduction can be a 10%, 20%, 30%, 40%, 50%, 60%, 70%, 80%, 90%, or 100%, or any percent reduction in between 10% and 100% as compared to native or control levels. It is understood that treatment does not necessarily refer to a cure or complete ablation of the disease, condition, or symptoms of the disease or condition.

As used herein, the terms prevent, preventing, and prevention of a disease or disorder refer to an action, for example, administration of a composition or therapeutic agent, that occurs before or at about the same time a subject begins to show one or more symptoms of the disease or disorder, which inhibits or delays onset or severity of one or more symptoms of the disease or disorder.

As used herein, references to decreasing, reducing, or inhibiting include a change of 10%, 20%, 30%, 40%, 50%, 60%, 70%, 80%, 90%, or greater as compared to a control level. Such terms can include, but do not necessarily include, complete elimination.

As used herein, subject means both mammals and non-mammals. Mammals include, for example, humans; non-human primates, e.g., apes and monkeys; cattle; horses; sheep; rats; mice; pigs; and goats. Non-mammals include, for example, fish and birds.

Throughout this application, various publications are referenced. The disclosures of these publications in their entireties are hereby incorporated by reference into this application.

The examples below are intended to further illustrate certain aspects of the methods and compounds described herein, and are not intended to limit the scope of the claims.

EXAMPLES

Example 1: Synthesis

A synthetic scheme for 4-(3,4-dichlorophenyl)-3-methyl-1H-pyrazol-5-amine, a precursor used to prepare the compounds described herein, is provided in Scheme 1.

Scheme 1:

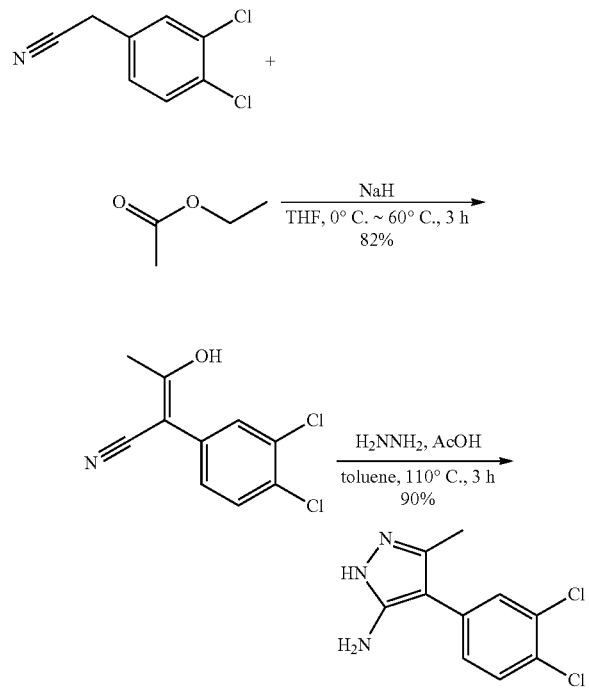

A synthetic scheme for Compounds C-5 and C-15 is shown in Scheme 2.

Scheme 2:

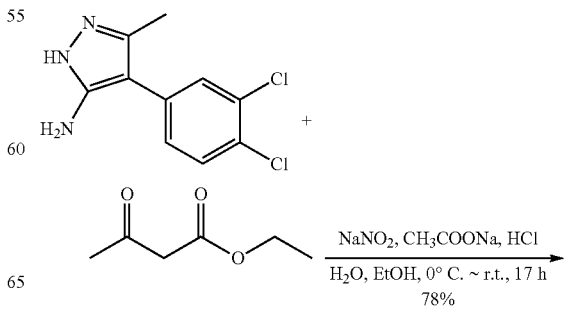

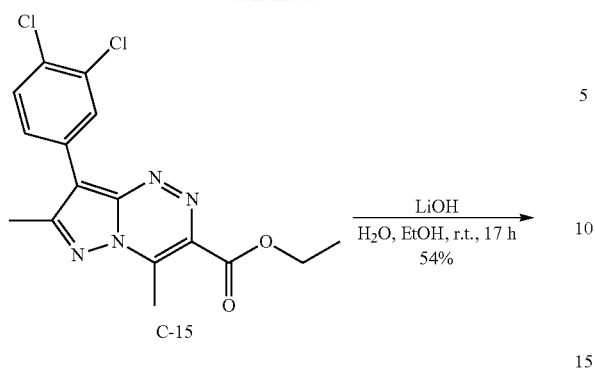
C-15
LiOH
H₂O, EtOH, r.t., 17 h
54%
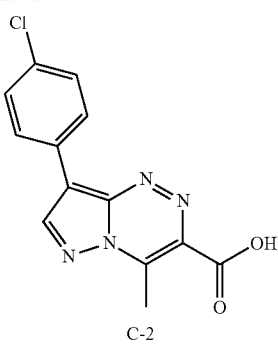
C-2
A synthetic scheme for Compound C-22 is shown in Scheme 4.
Scheme 4:
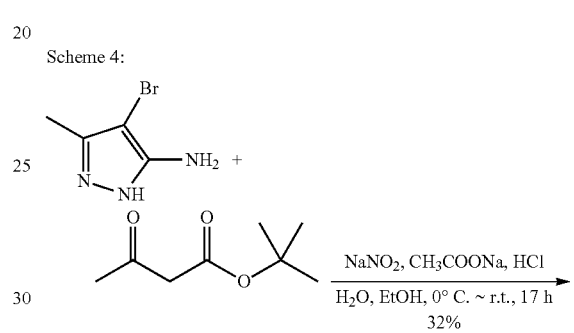
NaNO₂, CH₃COONa, HCl
H₂O, EtOH, 0° C. ~ r.t., 17 h
32%
C-5
A synthetic scheme for Compounds C-12 and C-2 is shown in Scheme 3.
Scheme 3:
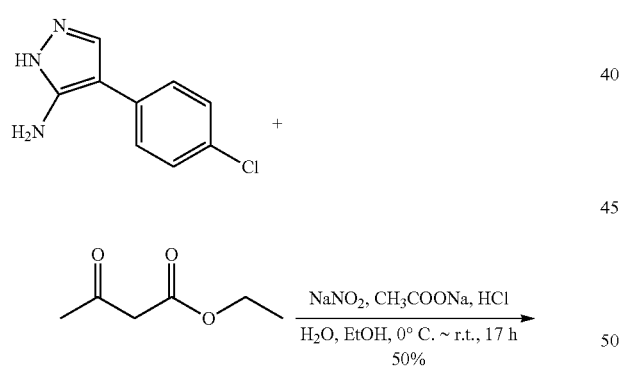
NaNO₂, CH₃COONa, HCl
H₂O, EtOH, 0° C. ~ r.t., 17 h
50%
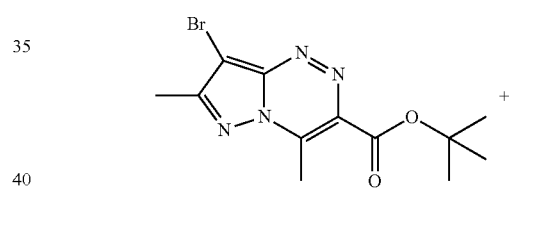
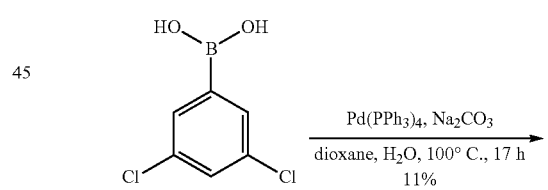
Pd(PPh₃)₄, Na₂CO₃
dioxane, H₂O, 100° C., 17 h
11%
LiOH
H₂O, EtOH, r.t., 17 h
40%
C-12
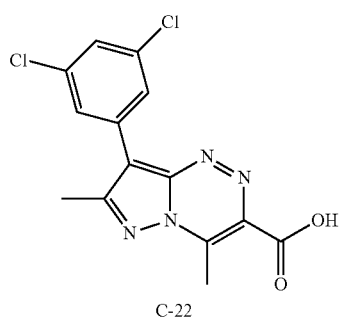
C-22
A synthetic scheme for Compound C-25 is shown in Scheme 5.

Scheme 5:

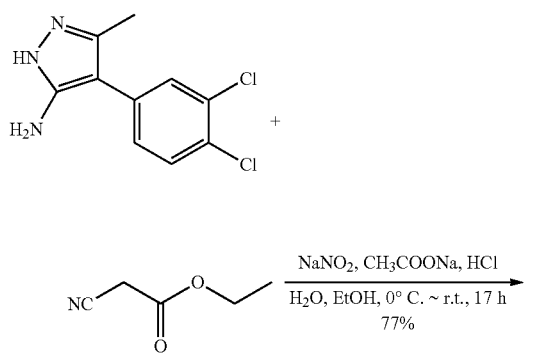

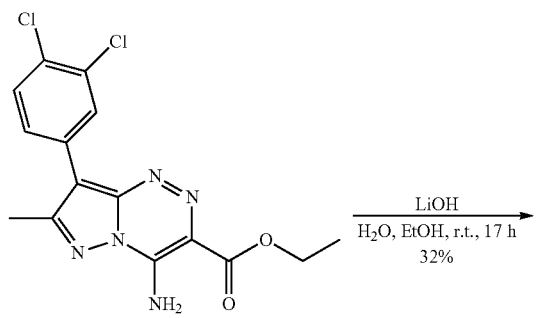

A synthetic scheme for Compound C-59 is shown in Scheme 6.

Scheme 6:

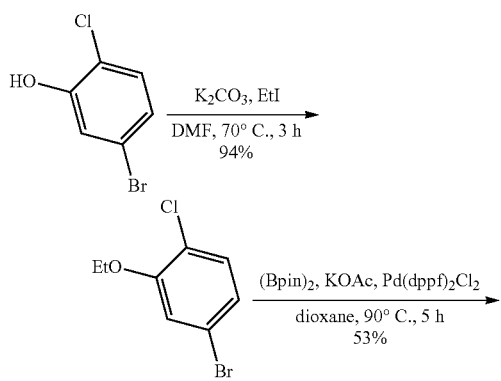

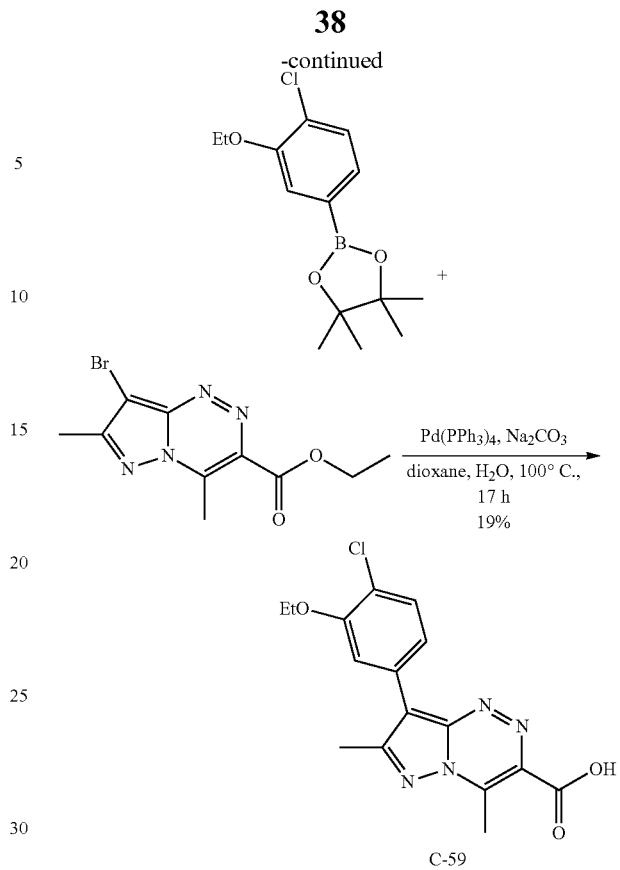

Example 2: Compound Profiling

A schematic showing a general approach for profiling the CFTR corrector drugs described herein is shown in FIG. 1. The compounds were initially subjected to the SPQ halide-sensitive fluorescence dye profiling assay for rescue or correction of membrane chloride ion permeability or transport with an 8-point concentration-response curve. The $EC_{50}$ values for the compounds described herein were determined and compared to the efficacy of the industry standard Vertex 809 (VX-809; Vertex Pharmaceuticals, Cambridge, Mass.) at 3 μM, which is the maximally effective profiling dose for VX-809 (Table 1). The VX-809 dosage at 3 μM was treated as having 100% efficacy in the comparison. Those compounds that showed superior potency and efficacy to VX-809 (i.e., Compounds C-2, C-5, C-12, C-15, C-22, C-25, C-55, C-59, and C-73) were subjected to both Ussing chamber electrophysiology and biochemical correction bioassays for further profiling.

TABLE 1

| Compound ID | $EC_{50}$ (μM) | % Efficacy | Efficacy Comparison to 3 μM VX-809 |
| --- | --- | --- | --- |
| C-1 | 1.9 | 200 | — |
| C-2 | 1.0 | 170 | 10-fold greater than VX-809 |
| C-3 | 11.5 | 200 | Equivalent to VX-809 |
| C-4 | No effect | 0 | N/A |
| C-5 | 0.1 | 160 | 10-fold greater than VX-809 |
| C-6 | 9.9 | 170 | 3-fold greater than VX-809 |
| C-7 | 7 | 220 | 3-fold greater than VX-809 |
| C-8 | 5.7 | 155 | 2-fold greater than VX-809 |
| C-9 | 17.8 | 120 | Less than VX-809 |
| C-10 | No effect | 40 | N/A |

TABLE 1-continued

| Compound ID | EC$_{50}$ (µM) | % Efficacy | Efficacy Comparison to 3 µM VX-809 |
|---|---|---|---|
| C-11 | No effect | 0 | N/A |
| C-12 | 1.0 | 120 | 7-fold greater than VX-809 |
| C-13 | No effect (toxic) | 0 | N/A |
| C-14 | No effect | 0 | N/A |
| C-15 | 0.3 | 120 | 10-fold greater than VX-809 |
| C-16 | 2.2 | 80 | 2-fold greater than VX-809 |
| C-17 | >30 | 75 | Equivalent to VX-809 |
| C-18 | 3.1 | 20 | Less than VX-809 |
| C-19 | No effect | 0 | N/A |
| C-20 | 2.0 | 100 | 2.5-fold greater than VX-809 |
| C-21 | 1.1 | 50 | 2.5-fold greater than VX-809 |
| C-22 | 1.3 | 130 | 12-fold greater than VX-809 |
| C-23 | Not determined (no plateau) | 110 | Equivalent to VX-809 |
| C-24 | 14.2 | 140 | Equivalent to VX-809 |
| C-25 | 0.83 | 100 | 10-fold greater than VX-809 |
| C-26.1 | No effect (toxic at 10 µM and above) | 0 | N/A |
| C-26.2 | No effect (toxic at 10 µM and above) | 0 | N/A |
| C-27 | 3.3 | 90 | 2-fold greater than VX-809 |
| C-28.1 | No effect | 0 | N/A |
| C-29 | No effect | 0 | N/A |
| C-30 | 26.3 | 50 | Less than VX-809 |
| C-31 | No effect | 0 | N/A |
| C-32 | 6 | 160 | 2.5-fold greater than VX-809 |
| C-32.1 | No effect (toxic at 10 µM and above) | 5 | N/A |
| C-34 | 0.58 (may be toxic at 10 µM and above) | 0 | N/A |
| C-35 | 0.7 | 100 | Equivalent to VX-809 |
| C-36 | 4.8 | 50 | Equivalent to VX-809 |
| C-37 | 5.1 | 80 | Equivalent to VX-809 |
| C-40 | No effect (toxic at 10 µM and above) | 0 | N/A |
| C-41 | No effect | 0 | N/A |
| C-42 | No effect | 5 | N/A |
| C-43 | 11 | 50 | Equivalent to VX-809 |
| C-45 | 2.5 | 50 | Equivalent to VX-809 |
| C-49 | 2 | 50 | Equivalent to VX-809 |
| C-50 | 0.5 | 30 | Equivalent to VX-809 |
| C-51 | 3.4 | 50 | Equivalent to VX-809 |
| C-52 | 20 | 70 | Less than VX-809 |
| C-53 | Not determined (no plateau) | 75 | Less than VX-809 |
| C-54 | 6.7 | 125 | 2-fold greater than VX-809 |
| C-55 | 0.66 | 100 | 10-fold greater than VX-809 |
| C-56 | 11.6 | 20 | Less than VX-809 |
| C-57 | 12.0 | 20 | N/A |
| C-58 | Not determined | 100 | N/A |
| C-59 | 0.16 | 110 | 15-fold greater than VX-809 |
| C-59.1 | 10.5 | 40 | Less than VX-809 |
| C-60 | No effect | 0 | N/A |
| C-66 | Not determined | 25 | N/A |
| C-66.1 | No effect | 0 | N/A |
| C-66.2 | 11 | 100 | — |
| C-68 | Not determined | 25 | N/A |
| C-68.1 | Not determined | 20 | N/A |
| C-70 | 3.7 | 110 | 2-fold greater than VX-809 |
| C-71 | 6.9 | 130 | Equivalent to VX-809 |
| C-71.1 | Not determined (toxic) | 0 | N/A |
| C-72 | 2.3 | 90 | — |
| C-72.1 | — | — | — |
| C-73 | 1.1 | 125 | 5-fold greater than VX-809 |
| C-73.1 | Not determined (toxic) | −75 | N/A |
| C-74 | — | — | — |

Example 3: SPQ High Throuput Screening Assay

To perform the SPQ high throughput screening assay, CFBE41o− cells were seeded into 96-well microtiter plates and were loaded with the fluorescent halide-sensitive dye, SPQ, in serum-containing culture medium. Certain wells were loaded with known positive control corrector molecules, including VX-809. The test compounds were loaded into wells and were tested in triplicate wells at a 10 µM dose and incubated over 48 hours at room temperature. During the 48 hour period, SPQ was absorbed. Plates were washed in a sodium chloride (NaCl) based Ringer and read once over two minutes to set the baseline SPQ fluorescence activity. Then, NaCl was replaced by sodium nitrate (NaNO$_3$) based Ringer. The plates were read twice over four minutes. The primary high throughput screen (HTS) data were analyzed to detect any function of rescued delF508-CFTR under basal conditions. The plate was read up to two times to complete the SPQ HTS assay.

Example 4: CFTR Western Blot

The method described in Example 3 was repeated with doses of the test compound of 0.01 µM, 0.1 µM, 1 µM, 10 µM, and 50 µM in Dulbecco's Modified Eagle Medium (DMEM) with 10% fetal bovine serum (FBS) for 48 hours at 37° C. Unaltered CFBE41o− cells were used as the model. A Western blot analysis of the lysates (10-50 µg total protein) was performed using the MM13-4 antibody for human CFTR to monitor changes in the CFTR protein. The most effective concentrations and time courses (12-96 h) were determined. By way of example, graphs showing the dose response results for exemplary compounds are provided in FIGS. 2-5. VX-809 and DMSO were used as the controls.

CFTR was immunoprecipitated under mild detergent conditions (1% digitonin, 2.5 mM HEPES, 10.0 mM CaCl$_2$, pH 7.6). The isolated protein complexes were run on SDS-PAGE gels and analyzed by mass spectroscopy. The CFBE41o− control cells were lysed in 2% digitonin (2.5 mM HEPES, 10.0 mM CaCl$_2$, pH 7.6). All lysis buffers were supplemented with a protease inhibitor cocktail (Complete Mini, Roche, Nutley, N.J.). CFTR was immunoprecipitated using Protein A-immobilized agarose beads and antibodies to the C-terminus of CFTR or to the second nucleotide-binding domain. The antibodies were covalently coupled to agarose beads before use (PROFOUND Mammalian Co-IP Kit, Pierce, Rockford, Ill.). The immunoprecipitated CFTR complexes were run on gels, and the interacting proteins were analyzed by mass spectroscopy.

Cells were lysed in RIPA buffer (50 mM Tris-HCl, pH 7.4, 150 mM NaCl, 1% NP-40, 0.5% Deoxycholic Acid, 0.1% SDS) plus a cocktail of protease inhibitors (Roche; Basel, Switzerland). Protein concentrations in the cell lysates were measured by BCA Protein Assay using BSA as standard (Pierce; Rockford, Ill.). Proteins (25 µg) were resolved on an 8% SDS-PAGE gel and transferred to PDVF membranes. Total CFTR in the lysate was detected by immunoblotting using a specific CFTR antibody (MM13-4 from Upstate, 1:500 dilution).

The compounds were then subjected to a biochemical assay to define which hit compounds rescued the band B core glycosylated endoplasmic reticulum (ER) form of delF508-CFTR within the cell interior into the maturely glycosylated band C form within the secretory pathway for proteins and within the plasma membrane. Effective compounds stabilized the band B form of CFTR and caused more of this form to accumulate at the level of the ER. The most effective compounds caused the band C form to appear.

By way of example, the delF508-CFTR mutation can be rescued from the ER with low temperature incubation for 48 hours (see examples in the blots as the positive control). The DMSO control is the simulated CF condition where the delF508-CFTR-expressing cells were grown at physiological temperature.

Figure 6:
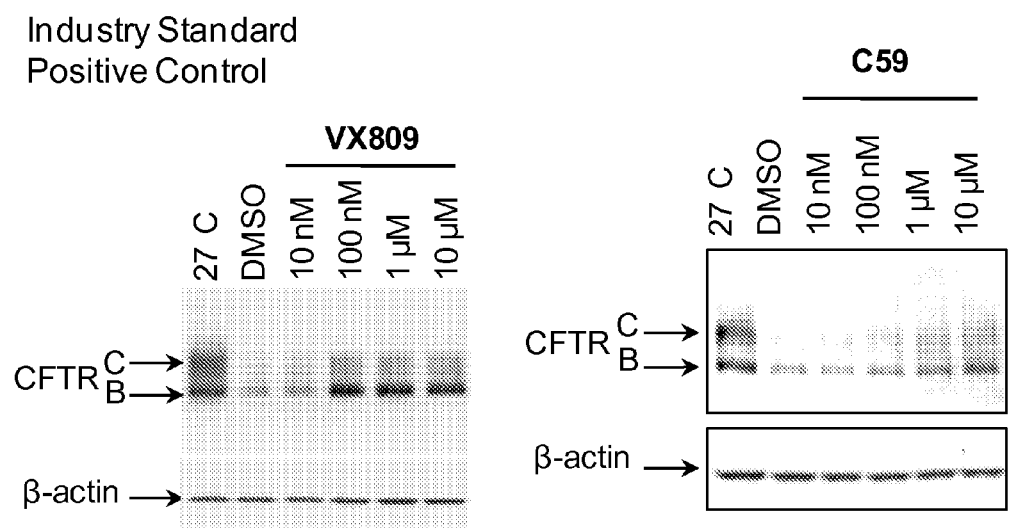
FIG. 6 is a Western blot demonstrating the delF508 CFTR rescue in CF human airway epithelial cells using Compound C-59 (right panel) and industry standard VX-809 (left panel) at increasing dosages (i.e., 10 nM, 100 nM, 1 μM, and 10 μM). DMSO and low temperature (27° C.) served as the controls.
Figure 7:
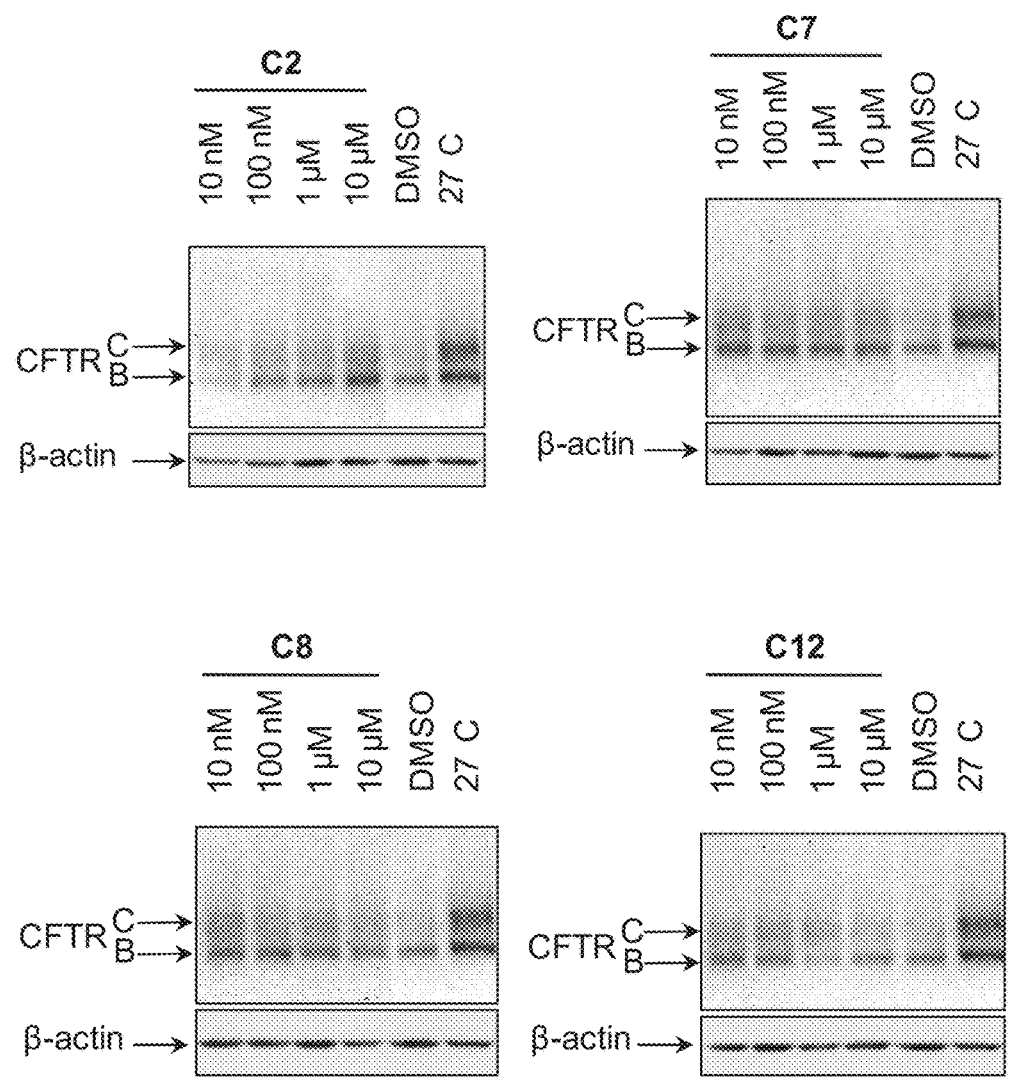
FIG. 7 is a Western blot demonstrating the delF508 CFTR rescue in CF human airway epithelial cells using Compounds C-2, C-7, C-8, and C-12 at increasing dosages (i.e., 10 nM, 100 nM, 1 μM, and 10 μM). DMSO and low temperature (27° C.) served as the controls.
Figure 8:
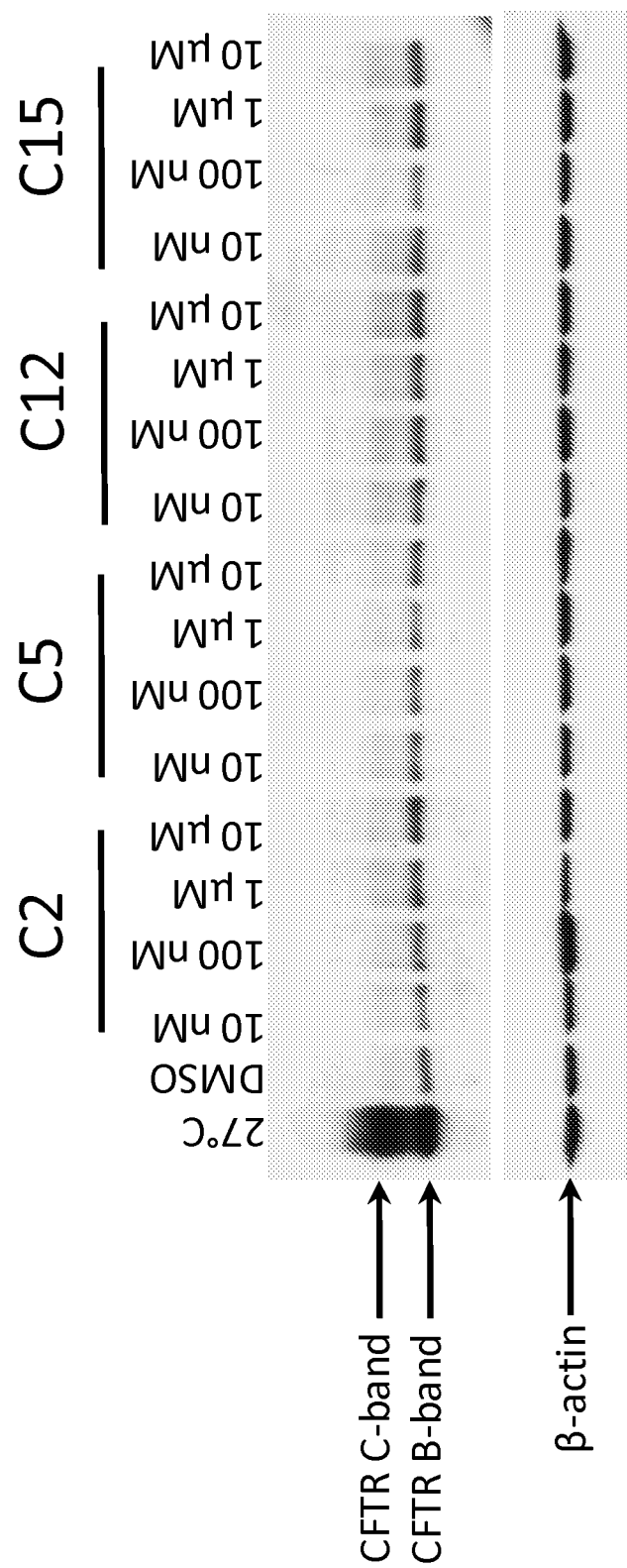
FIG. 8 is a Western blot demonstrating the delF508 CFTR rescue in CF human airway epithelial cells using Compounds C-2, C-5, C-12, and C-15 at increasing dosages (i.e., 10 nM, 100 nM, 1 μM, and 10 μM). DMSO and low temperature (27° C.) served as the controls.

Certain compounds described herein were also tested in the biochemical rescue assay. Each compound was tested at 10 µM, 1 µM, 10 nM, and 100 nM. DMSO, VX-809 treated cells, WT-CFTR expressing cells, and low temperature (27° C.) corrected cells served as the controls. See FIGS. 6-8. The experiments were performed in 10% serum containing medium using the method as described above. The data demonstrate that the corrector compounds described herein are effective independent of serum protein. Specifically, Compounds C-2, C-12, and C-15 showed biochemical correction of the delF508-CFTR protein in CF human airway epithelial cells.

Example 5: Electrical Measurements

Figure 9:
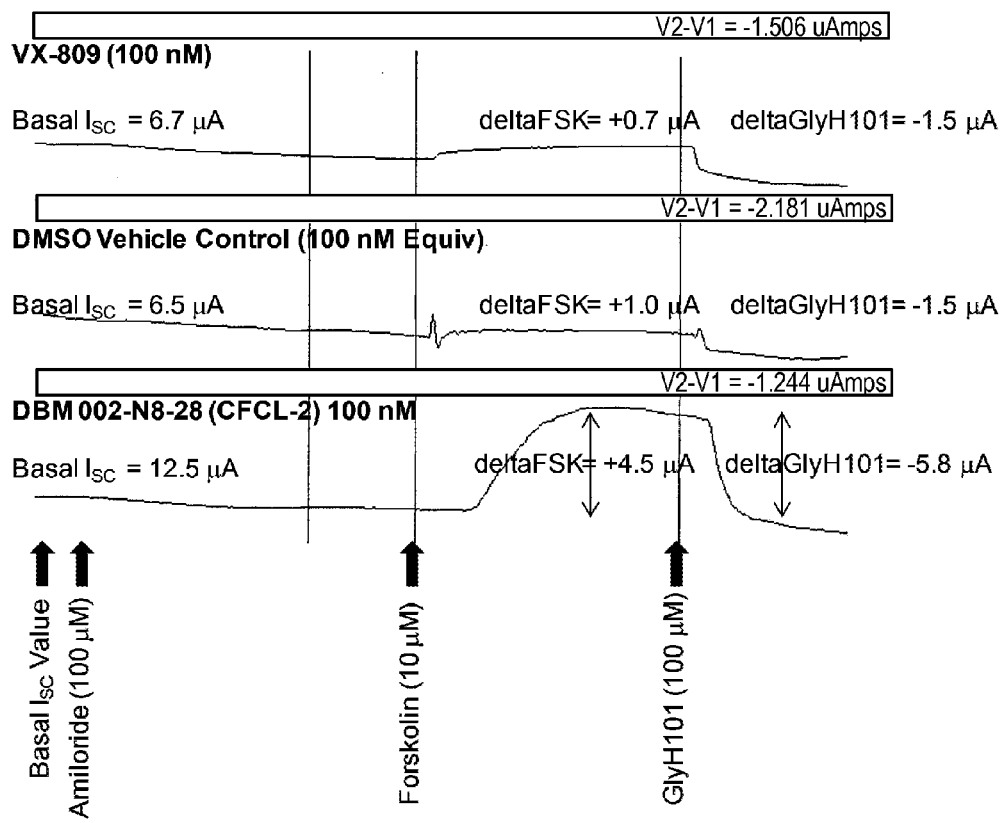
FIG. 9 is a schematic of an exemplary Ussing chamber-derived short-circuit current trace illustrating the correction of functional apical membrane-resident delF508-CFTR chloride ion channels in a high-resistance CF human airway epithelial cell monolayer with VX-809 (100 nM), DMSO (100 nM) and an existing CFTR corrector (CFCL-2).

An electrical assay was also performed to determine the functional rescue of delF508-CFTR to the apical cell membrane in a polarized epithelium using the compounds described herein. The metrics analyzed were the basal short-circuit Cl⁻ current, the change or delta Cl⁻ current stimulated by forskolin, the total stimulated Cl⁻ current (basal and forskolin), and the change or delta Cl⁻ current inhibited by GlyH101. For exemplary purposes, DMSO (100 nM) and VX-809 (100 nM equivalent) treatments were controls, and a CFCL corrector was tested (see FIG. 9).

Only high-resistance cell monolayers (>800 to 1,000 Ohms per cm$^2$) were used in the experiments. Basal short-circuit current ($I_{SC}$) was measured and documented. Amiloride was added to the apical side of the Ussing chamber to block any contribution of ENaC or other sodium or cation channels under basal or stimulated conditions. The effect of amiloride was negligible under these cell culture conditions. In the continued presence of amiloride (100 µM), forskolin (10 µM) was added to both sides of the monolayer to selectively open any delF508-CFTR chloride channels in the apical cell membrane. This activation step uncovered any remaining corrected delF508-CFTR chloride ion channels in the apical membrane of the polarized CF human bronchial epithelium. The final step was the addition of a CFTR-selective inhibitor, GlyH101 (100 µM), to reverse the effect of forskolin. The inhibitor also blocked some of the basally active current, validating that it is CFTR-driven current.

Figure 10:
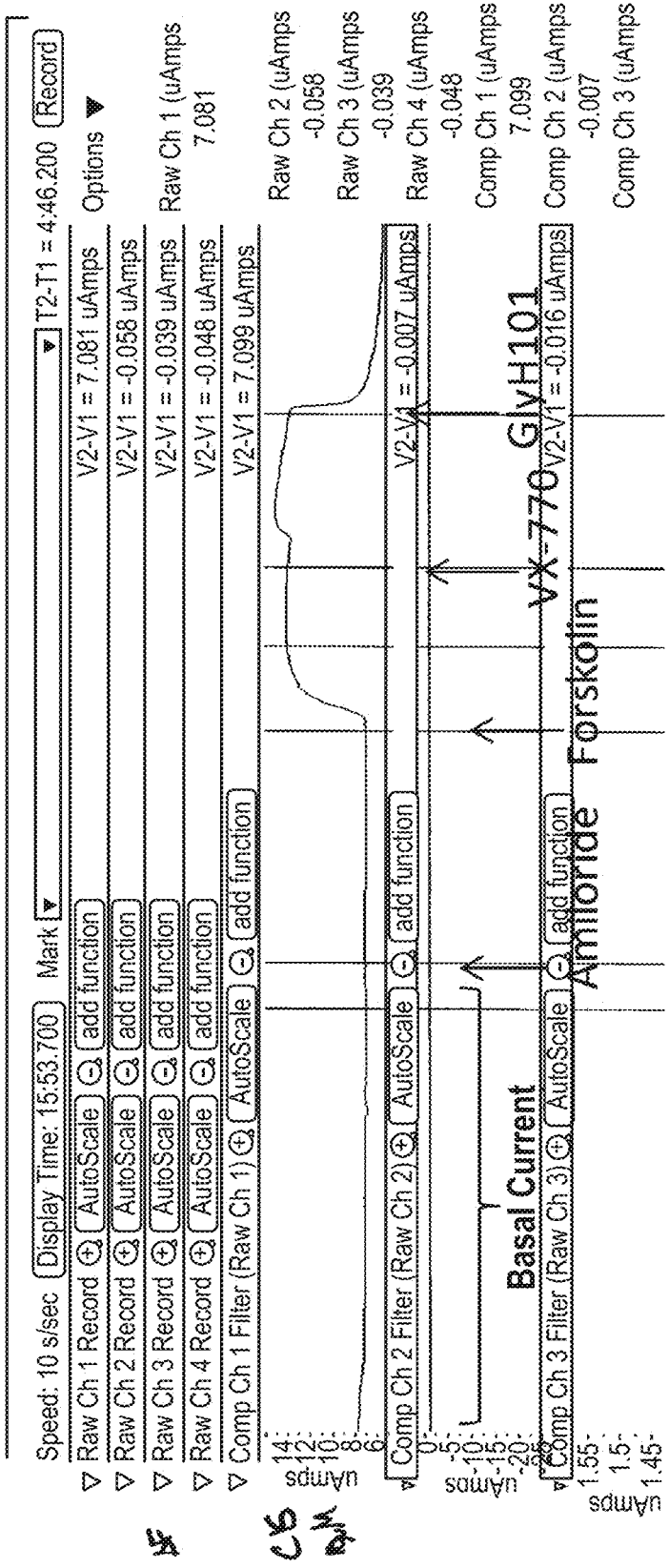
FIG. 10 is a schematic of an Ussing chamber-derived short-circuit current trace illustrating the correction of functional apical membrane-resident delF508-CFTR chloride ion channels in a high-resistance CF human airway epithelial cell monolayer with Compound C-15.
Figure 11:
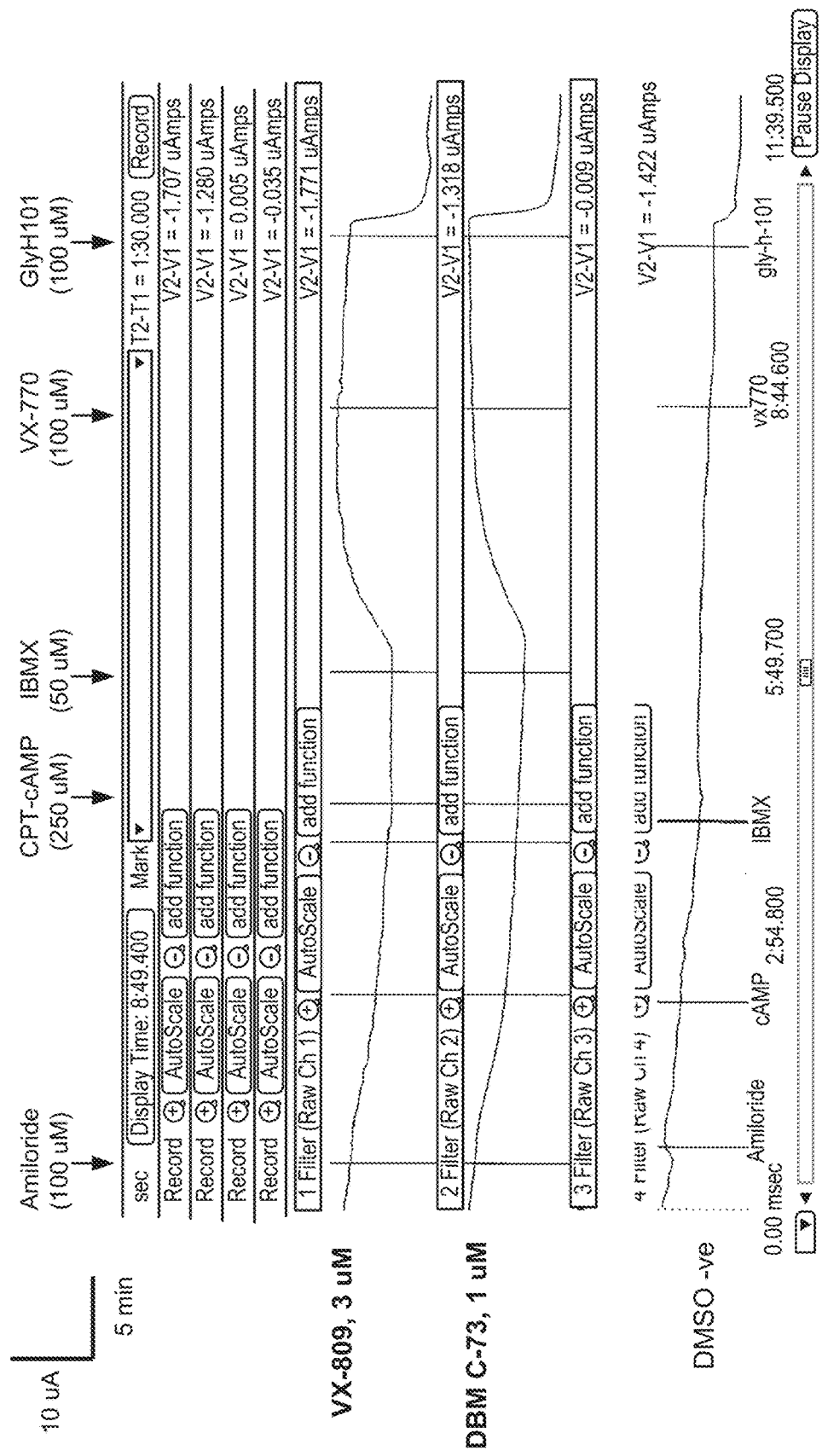
FIG. 11 is a schematic of an Ussing chamber-derived short-circuit current trace illustrating the correction of functional apical membrane-resident delF508-CFTR chloride ion channels in a high-resistance CF human airway epithelial cell monolayer with Compound C-73.
Figure 12:
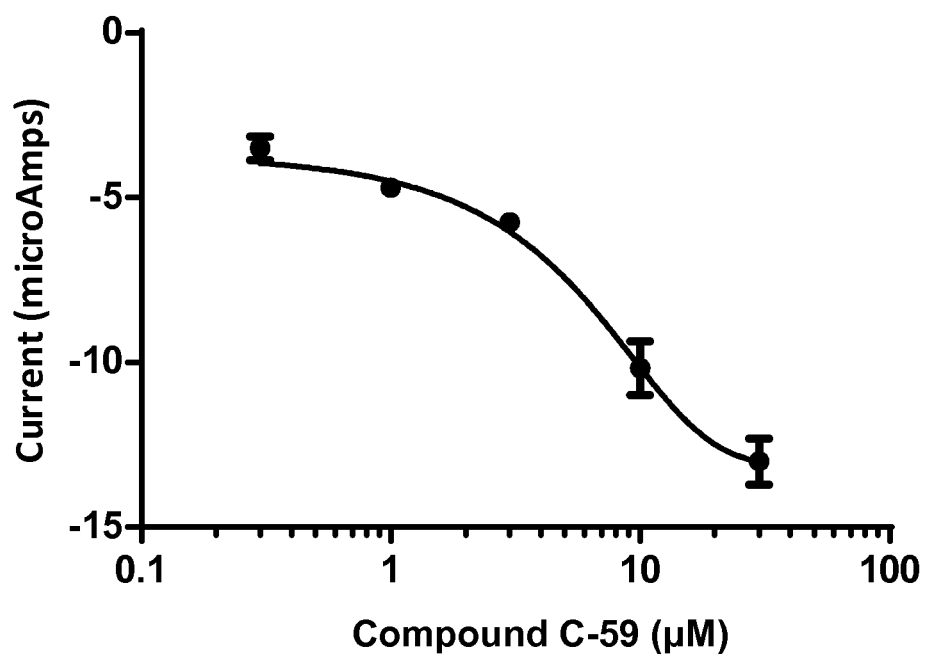
FIG. 12 shows the results from the GlyH101-sensitive current analysis in a concentration-response curve plot for Compound C-59.

Ussing chamber-derived short-circuit current data were obtained for Compounds C-15 and C-73 (see FIGS. 10 and 11). Compound C-15 shows robust correction of functional delF508-CFTR chloride ion channels in the apical membrane of a polarized CF human bronchial epithelium (see FIG. 10). Furthermore, FIG. 10 demonstrates that the Vertex CFTR potentiator compound, VX-770 (Kalydeco), opens some additional delF508-CFTR channels in the presence of forskolin. This indicates that the currents are carried by CFTR channels. Compound C-73 showed superior potency and equivalent to greater efficacy versus VX-809. The same protocol of additions of drugs to the apical side of the Ussing chamber was performed on each cell monolayer as described above. Final concentrations of drugs are shown in FIG. 11. CPT-cAMP and IBMX are equivalent and CFTR-specific agonists to forskolin. As described above, VX-770 is a CFTR potentiator drug added to activate any remaining corrected CFTR present. The concentration-response curve plot for Compound C-59 shows that increasing concentrations of Compound C-59 (x-axis) stimulate increased amounts of GlyH101-sensitive current (see FIG. 12).

The compounds and methods of the appended claims are not limited in scope by the specific compounds and methods described herein, which are intended as illustrations of a few aspects of the claims and any compounds and methods that are functionally equivalent are within the scope of this disclosure. Various modifications of the compounds and methods in addition to those shown and described herein are intended to fall within the scope of the appended claims. Further, while only certain representative compounds, methods, and aspects of these compounds and methods are specifically described, other compounds and methods are intended to fall within the scope of the appended claims. Thus, a combination of steps, elements, components, or constituents can be explicitly mentioned herein; however, all other combinations of steps, elements, components, and constituents are included, even though not explicitly stated.

What is claimed is:

1. A compound of the following formula:

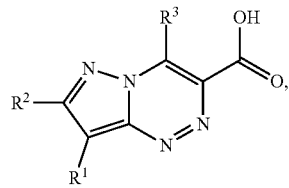

or a pharmaceutically acceptable salt thereof, wherein:

$R^1$ is substituted aryl;

$R^2$ is hydrogen, substituted or unsubstituted alkyl, or substituted or unsubstituted aryl; and $R^3$ is hydrogen, substituted or unsubstituted alkyl, substituted or unsubstituted amino, or substituted carbonyl, wherein when $R^2$ is hydrogen and $R^3$ is methyl, then $R^1$ is not p-chlorophenyl.

2. A compound of the following formula:

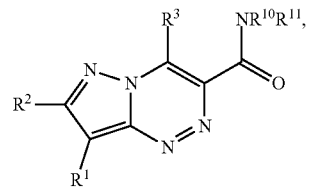

or a pharmaceutically acceptable salt thereof, wherein $R^1$ is substituted aryl;

$R^2$ is hydrogen, substituted or unsubstituted alkyl, or substituted or unsubstituted aryl;

$R^3$ is hydrogen, substituted or unsubstituted alkyl, substituted or unsubstituted amino, or substituted carbonyl; and $R^{10}$ and $R^{11}$ are each independently selected from the group consisting of hydrogen and substituted or unsubstituted alkyl.

3. A compound of the following formula:

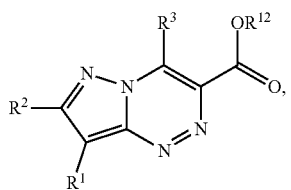

or a pharmaceutically acceptable salt thereof, wherein
 $R^1$ is substituted aryl;
 $R^2$ is hydrogen, substituted or unsubstituted alkyl, or substituted or unsubstituted aryl;
 $R^3$ is hydrogen, substituted or unsubstituted alkyl, substituted or unsubstituted amino, or substituted carbonyl; and
 $R^{12}$ is hydrogen, substituted or unsubstituted alkyl, or substituted or unsubstituted cycloalkyl,
 wherein when $R^2$ is hydrogen and $R^3$ is methyl, then $R^1$ is not p-chlorophenyl.

4. A compound selected from the group consisting of:

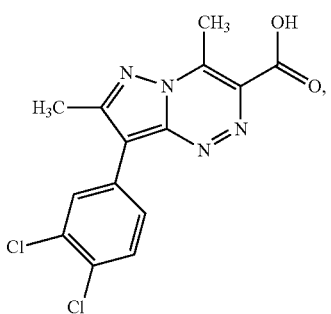

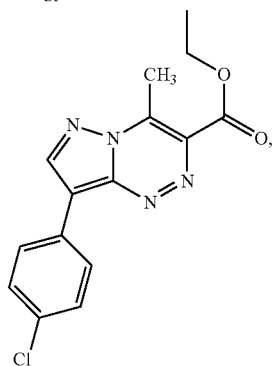

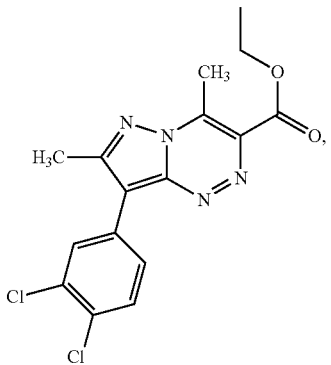

-continued

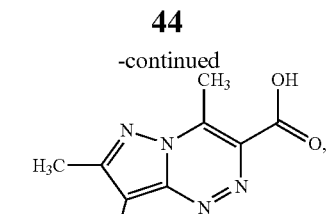

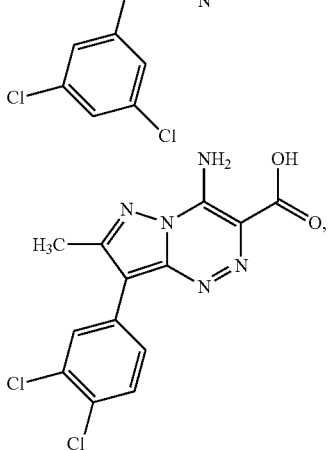

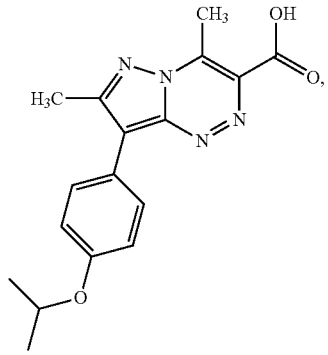

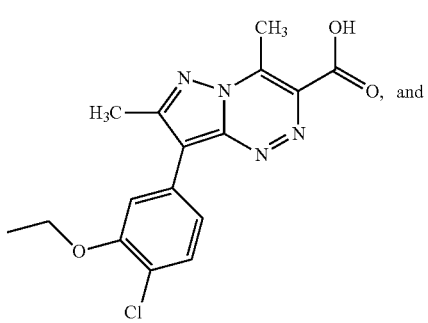

and

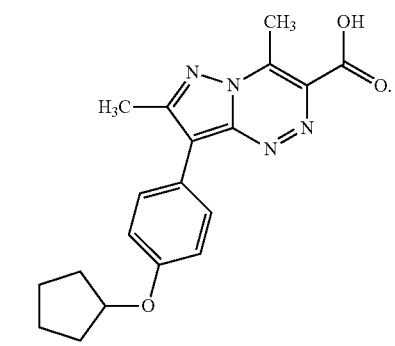

5. A compound of the following formula:

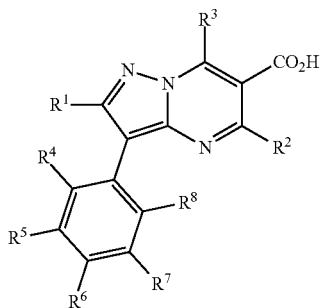

or a pharmaceutically acceptable salt thereof, wherein:
$R^1$, $R^2$, and $R^3$ are each independently selected from the group consisting of hydrogen and substituted or unsubstituted alkyl; and
$R^4$, $R^5$, $R^6$, $R^7$, and $R^8$ are each independently selected from the group consisting of hydrogen, halogen, hydroxyl, substituted or unsubstituted alkyl, and substituted or unsubstituted aryl.

6. The compound of claim 5, wherein the compound is

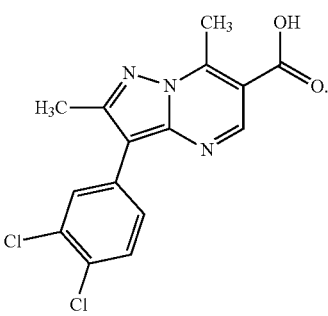 [SMILES: Cc1nn2c(C)c(C(=O)O)cnc2c1-c1ccc(Cl)c(Cl)c1]

7. A compound of the following formula:

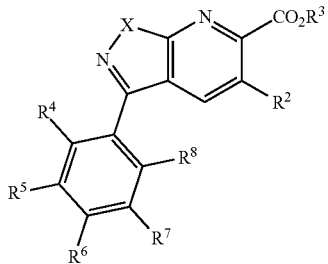

or a pharmaceutically acceptable salt thereof, wherein:
X is O or $NR^1$, wherein $R^1$ is hydrogen or substituted or unsubstituted alkyl;

$R^2$ is hydrogen;
$R^3$ is hydrogen, substituted or unsubstituted alkyl, or substituted or unsubstituted cycloalkyl; and
$R^4$, $R^5$, $R^6$, $R^7$, and $R^8$ are each independently selected from the group consisting of hydrogen, halogen, hydroxyl, substituted or unsubstituted alkyl, and substituted or unsubstituted aryl.

8. A composition comprising the compound of claim 1 and a pharmaceutically acceptable carrier.

9. A method for the treatment of a protein folding disorder in a subject, comprising:
administering to the subject an effective amount of a compound of claim 1.

10. The method of claim 9, wherein the protein folding disorder is cystic fibrosis.

11. A method of rescuing halide efflux in a cell, comprising:
contacting a cell with a compound of claim 1, wherein the cell endogenously expresses a CFTR mutation.

12. The method of claim 11, wherein the CFTR mutation is delF508-CFTR.

13. The method of claim 11, wherein the halide efflux is chloride efflux.

14. A method of correcting a processing defect of a delF508-CFTR protein in a cell, comprising:
contacting a cell with a compound of claim 1, wherein the cell expresses a delF508-CFTR mutation.

15. The method of claim 11, wherein the cell is a CF human airway epithelial cell.

16. The method of claim 11, wherein the cell is a CF human lung.

17. A method of correcting functional delF508-CFTR chloride channels in a cell, comprising:
contacting a cell with a compound of claim 1, wherein the cell is a polarized epithelial cell.

18. The method of claim 11, wherein the method is performed in vitro.

19. The method of claim 11, wherein the method is performed in vivo.

20. The compound of claim 1, wherein the compound has the following structure:

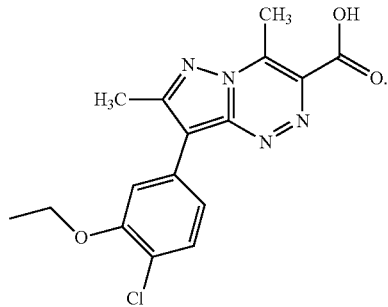

* * * * *